US008627243B1

(12) United States Patent
Lin et al.

(10) Patent No.: US 8,627,243 B1
(45) Date of Patent: Jan. 7, 2014

(54) METHODS FOR OPTIMIZING CONDUCTOR PATTERNS FOR ECP AND CMP IN SEMICONDUCTOR PROCESSING

(71) Applicant: Taiwan Semiconductor Manufacturing Company, Ltd., Hsin-Chu (TW)

(72) Inventors: Chi-Feng Lin, Hsin-Chu (TW); Yu-Wei Chou, Hsin-Chu (TW); Wen-Cheng Huang, Changhua (TW); Cheng-I Huang, Hsin-Chu (TW); Ching-Hua Hsieh, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/650,783

(22) Filed: Oct. 12, 2012

(51) Int. Cl.
| G06F 17/50 | (2006.01) |
|---|---|
| G06F 19/00 | (2011.01) |
| G01R 31/26 | (2006.01) |
| G01L 21/00 | (2006.01) |
| G01N 37/00 | (2006.01) |
| G01B 7/26 | (2006.01) |
| G01B 5/18 | (2006.01) |
| G01B 11/22 | (2006.01) |
| G01B 13/14 | (2006.01) |
| G06F 11/30 | (2006.01) |

(52) U.S. Cl.
CPC ............ *G06F 17/5081* (2013.01); *G06F 19/00* (2013.01); *G06F 11/30* (2013.01); *G01B 13/14* (2013.01); *G01N 37/00* (2013.01); *G01B 7/26* (2013.01); *G01B 5/18* (2013.01); *G01B 11/22* (2013.01)
USPC ................ 716/54; 716/55; 716/51; 716/112; 716/52; 700/110; 700/120; 700/121; 703/2; 703/14; 702/81; 702/166; 702/170; 702/182; 438/14; 438/800

(58) Field of Classification Search
CPC ..... G06F 17/5081; G06F 19/00; G06F 11/30; G01R 31/26; H01L 21/66; G01N 37/00; G01B 7/26; G01B 5/18; G01B 11/22; G01B 13/14
USPC .......... 716/54, 55, 51, 112, 52; 700/110, 120, 700/121; 702/81, 166, 170, 182; 703/2, 14; 438/14, 800
See application file for complete search history.

(56) References Cited

U.S. PATENT DOCUMENTS

| 7,197,737 B1* | 3/2007 | Iandolo et al. ................ 716/124 |
| 7,544,617 B1* | 6/2009 | Chandra et al. ............... 438/691 |

(Continued)

OTHER PUBLICATIONS

Yoon, Patent Document No. KR-2002056147A, abstract and drawing only, 3 pages.*

*Primary Examiner* — Phallaka Kik
(74) *Attorney, Agent, or Firm* — Slater & Matsil, L.L.P.

(57) ABSTRACT

Methods for optimizing conductor patterns for conductors formed by ECP and CMP processes. A method includes receiving layout data for an IC design where electrochemical plating (ECP) processes form patterned conductors in at least one metal layer over a semiconductor wafer; determining from the received layout data a global effects factor corresponding to a global pattern density; determining layout effects factors for unit grid areas corresponding to the pattern density of the at least one metal layer within the unit grid areas, determining local effects factors for each unit grid area; using a computing device, executing an ECP simulator using at least one of the global effects factor and the local effects factors, and using the layout effects factor; outputting an predicted post-ECP hump data map from the ECP simulator; and if indicated by a threshold comparison, modifying the layout data.

20 Claims, 11 Drawing Sheets

(56) References Cited

U.S. PATENT DOCUMENTS

| | | | |
|---|---|---|---|
| 7,801,717 B2* | 9/2010 | Chang et al. | 703/14 |
| 8,423,328 B2* | 4/2013 | Cohn et al. | 703/2 |
| 8,441,131 B2* | 5/2013 | Ryan | 257/774 |
| 2004/0115932 A1* | 6/2004 | Cheng et al. | 438/676 |
| 2004/0253810 A1* | 12/2004 | Wang et al. | 438/633 |
| 2005/0205961 A1* | 9/2005 | Doong | 257/499 |
| 2006/0073694 A1* | 4/2006 | Chang | 438/618 |
| 2008/0131796 A1* | 6/2008 | Werner et al. | 430/30 |
| 2008/0176343 A1* | 7/2008 | Chang et al. | 438/5 |
| 2010/0148235 A1* | 6/2010 | Toubou et al. | 257/296 |
| 2010/0261095 A1* | 10/2010 | Grant et al. | 430/5 |
| 2011/0077916 A1* | 3/2011 | Cohn et al. | 703/2 |
| 2011/0214101 A1* | 9/2011 | Cheng et al. | 716/136 |
| 2013/0061196 A1* | 3/2013 | Cheng et al. | 716/132 |
| 2013/0087907 A1* | 4/2013 | Lehr et al. | 257/737 |

* cited by examiner

METHODS FOR OPTIMIZING CONDUCTOR PATTERNS FOR ECP AND CMP IN SEMICONDUCTOR PROCESSING

BACKGROUND

As materials used in semiconductor processes advance, line spacing and line widths of conductors formed by electrochemical plating (ECP) and chemical-mechanical polishing (CMP) are reduced. When material is formed by ECP and CMP to form conductors, problems such as gap filling, voids and pattern resolution (poor line quality) may occur.

To form conductive patterns on a semiconductor substrate using ECP, for each one of several metal layers to be formed over the semiconductor substrate, a dielectric layer is deposited over the semiconductor substrate. Using photolithography a conductor pattern for the selected metal layer is formed in a photoresist layer formed over the dielectric layer. An etch step is then performed on the underlying dielectric layer using the patterned photoresist as an etch mask to form patterned trenches. After the dielectric layer is etched, the photoresist is removed.

ECP may then be performed to deposit the conductive material into the trenches. In ECP, the substrate with the patterned dielectric layer is placed in an electrolyte electroplating bath solution, for example to electroplate copper conductors; the bath is acid copper sulfate solution. A sacrificial anode and the semiconductor substrate are immersed in the solution with the semiconductor substrate electrically coupled to act as a cathode. An electric potential is applied and the copper conductor material is drawn to the substrate by current flowing between the anode and the cathode terminals, and the conductor material is electroplated filling the trenches. The ECP process continues until the trenches in the dielectric are filled, and then overfilled, with the conductor material. This is referred to as an "overburden".

CMP is then used to remove the overburden conductor material from the substrate surface until the upper surface of the dielectric layer is exposed between the trenches, and the patterned conductors then remain in the trenches within the dielectric layer. This ECP and CMP process is performed for each metal layer formed over the substrate.

Following the ECP and CMP processes, a uniform conductor thickness is desired with a planar upper surface. However, in actual practice the thickness uniformity of the conductor material following the ECP process (post-ECP) varies across the semiconductor substrate. The thickness of the ECP plated conductor layer is known to be affected by the conductor pattern being formed (pattern density). The pattern density causes non-uniform current density during plating, resulting in areas where the post-ECP thickness is higher than in other areas. When this higher thickness area is observed in a post-ECP inspection of the conductor material on the substrate, it is often called a "hump."

In semiconductor processing, the post-ECP and post-CMP results are examined using "hump data" maps of semiconductor wafers. The post-ECP hump data map illustrates areas on a semiconductor substrate that have non-uniform thickness in the conductor layer after the ECP (that is, the hump data map provides a visual representation of where the "humps" occur in the conductor thickness). Hump data maps may also be used after CMP processes (referred to as post-CMP hump data maps) to identify areas where the surface of the planarized dielectric and conductor material is non-uniform after CMP.

Recently computer simulation models for both the ECP and CMP processes have been developed. These simulators are referred to herein as virtual ECP (V-ECP) and virtual CMP (V-CMP). However, the predicted hump data maps obtained using the existing V-ECP simulators do not accurately track the actual post-ECP results obtained.

BRIEF DESCRIPTION OF THE DRAWINGS

For a more complete understanding of the illustrative embodiments, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the illustrative embodiments and are not necessarily drawn to scale.

DETAILED DESCRIPTION OF ILLUSTRATIVE EMBODIMENTS

Figure 1:
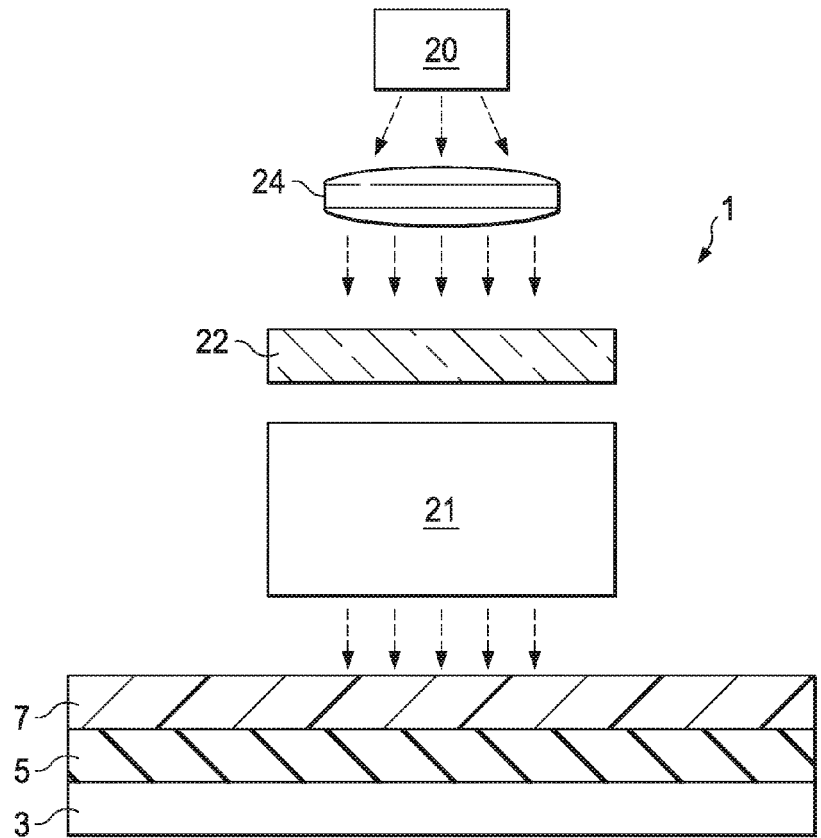
FIG. 1 depicts in a simplified cross-sectional view a portion of a semiconductor substrate in an photolithography process, for use in illustrating the embodiments.

The making and using of the illustrative example embodiments are discussed in detail below. It should be appreciated, however, that an illustrative embodiment provides many applicable inventive concepts that can be embodied in a wide variety of specific contexts. The specific embodiments discussed are merely examples used to describe specific ways to make and use the embodiments, and these examples do not limit the scope of this description and do not limit the scope of the appended claims.

As a brief summary, in one aspect, the present invention provides for a method, the method including receiving layout data for an IC design to be manufactured on a semiconductor wafer with patterned conductors formed in an electrochemical plating (ECP) process, and extracting layout data from the received layout data corresponding to at least one metal layer. The method further includes determining from the extracted layout data a layout effects factor for each of a plurality of unit grid areas covering the semiconductor wafer, the layout effects factor corresponding to one selected from a line edge density and a pattern density for the at least one metal layer in the unit grid area, and determining from the extracted layout data a global effects factor corresponding to a global pattern density for the at least one metal layer over a total area of the semiconductor wafer. The method further includes determining from the extracted layout data a local effects factor for each of the unit grid areas, the local effects factor corresponding to a local pattern density for the at least one metal layer over an area of the semiconductor wafer within a local grid area larger than, and surrounding, the corresponding unit grid area, and using a computing device, performing an ECP simulation configured to predict post-ECP plating hump heights in the at least one metal layer for each one of the unit grid areas, the ECP simulation using at least one of the global effects factor and the local effects factor as inputs, and using the layout effects factor as an input. The method further includes outputting a predicted post-ECP hump data map for the semiconductor wafer from the ECP simulation.

In another aspect, the present invention provides for a method, the method including using a computing device having a non-transitory computer memory storing executable programs, performing the steps of (a) retrieving layout data from the non-transitory computer memory for a design to be manufactured using an electrochemical plating (ECP) process forming patterned conductors in at least one metal layer over a semiconductor wafer, (b) determining from the layout data, for each one of a plurality of unit grid areas covering the semiconductor wafer, a layout effects factor corresponding to one selected from a line edge density and a conductor pattern density in the at least one metal layer in the unit grid area, (c) determining from the layout data a global effects factor corresponding to a total area of the metal layer on the semiconductor wafer over a total area of the semiconductor wafer, an (d) determining from the layout data a local effects factor for each of the unit grid areas, the local effects factor corresponding to a local pattern density of the at least one metal layer over a the surface area of a local area that is larger than and includes the corresponding unit grid area. The method further includes using the computing device, executing an ECP simulation using at least one of the global effects factor the local effects factor as inputs, and using the layout effects factor as an input, to determine a predicted post-ECP hump height of the at least one metal layer for each of the unit grid areas. The method further includes storing in the non-transitory computer memory a predicted post-ECP hump data map, and determining from the predicted post-ECP hump data map whether the at least one metal layer will have a post-ECP hump height on the semiconductor wafer that exceeds a predetermined post-ECP hump height threshold.

In yet other aspects, the present invention provides for a non-transitory computer readable medium containing executable instructions that, when executed by a computing device, cause the computing device to perform the following actions: retrieving layout data from the non-transitory computer readable medium for forming patterned conductors in at least one metal layer over a semiconductor wafer in an electrochemical plating (ECP) process; determining from the lout data a global effects factor corresponding to the total area in the at least one metal layer on the semiconductor wafer over a total area of the semiconductor wafer; determining from the layout data a layout effects factor for each of a plurality of unit grid areas covering the semiconductor wafer, the layout effects factor corresponding to the pattern density of the at least one metal layer; determining from the layout data a local effects factor for each unit grid area, each local effects factor corresponding to the total area of the at least one metal layer over the area of the semiconductor wafer in a local area that is larger than and includes the corresponding unit grid area using the computing device, executing an ECP simulation using at least one of the global effects factor and the local effects factor, and using the layout effects factor for each unit grid area, to predict the post-ECP hump height of the at least one metal layer for each unit grid area storing in the non-transitory computer readable medium an predicted post-ECP hump data map output from the ECP simulation; responsive to the post-ECP hump data map, modifying the layout for the at least one metal layer; and outputting a photomask generation file for the at least one metal layer.

In forming conductors for integrated circuits, several metallization layers are formed over the substrate, each separated from the adjacent metallization layers by interlevel dielectric material. These metallization layers are usually referred to in order starting from the surface of the substrate as metal 0, metal 1, etc. In forming the metallization layers, each metal level is formed using both ECP and CMP processes. The ECP process plates the conductor material for each metal layer into trenches formed in a corresponding intermetal dielectric layer, and the CMP process then removes excess overburden conductor material from the intermetal dielectric layer until the surface of the dielectric material is exposed. The finished conductors are conductor lines within filled trenches in the intermetal dielectric material. This series of process steps using ECP and CMP is performed for each metal layer metal 0, metal 1 etc. formed over the semiconductor substrate. The metal layers are separated vertically by interlevel dielectric layers. Copper is typically used as the conductor material, for example.

FIG. 1 depicts in a cross sectional view a photomask 22 (also referred to as a reticle) being used in a photolithography system 1 to form a pattern for a metal layer to be plated. The pattern from photomask 22 is transferred to a photoresist layer 7, which overlies a dielectric layer 5. Dielectric layer 5 is shown deposited on a semiconductor substrate 3. Dielectric layer 5 is formed from an appropriate intermetal dielectric material, such as high-k and low-k dielectric materials, silicon dioxide, oxide, nitrides and the like. Although a single dielectric layer 5 is shown over substrate 3 for simplicity in the illustration, in a practical device many intervening metal and interlevel dielectric layers are formed over substrate 3 and dielectric layer 5 includes these layers. A light source 20, which is selected from sources such as visible light or laser, or other energy source depending on the light sensitivity of the particular photoresist 7, is energized and the light energy is focused by lens 24 onto photomask 22. An imaging system 21 then is used to further focus the optical pattern from the photomask 22 onto the photoresist layer 7, thereby exposing the photoresist 7 through the pattern on mask 22. After the exposure of the photoresist 7 as shown in FIG. 1, the pattern on the photomask 22 creates exposed and unexposed areas in the photoresist layer 7 which correspond to the patterns on the photomask 22.

The photoresist 7 is then developed using a chemical developer, and the unexposed portion of photoresist 7 is removed, leaving a patterned photoresist layer 7. Etching of the dielectric layer 5 may then be performed using the patterned photoresist 7 as an etch mask. Photoresist 7 is then removed.

Figure 2:
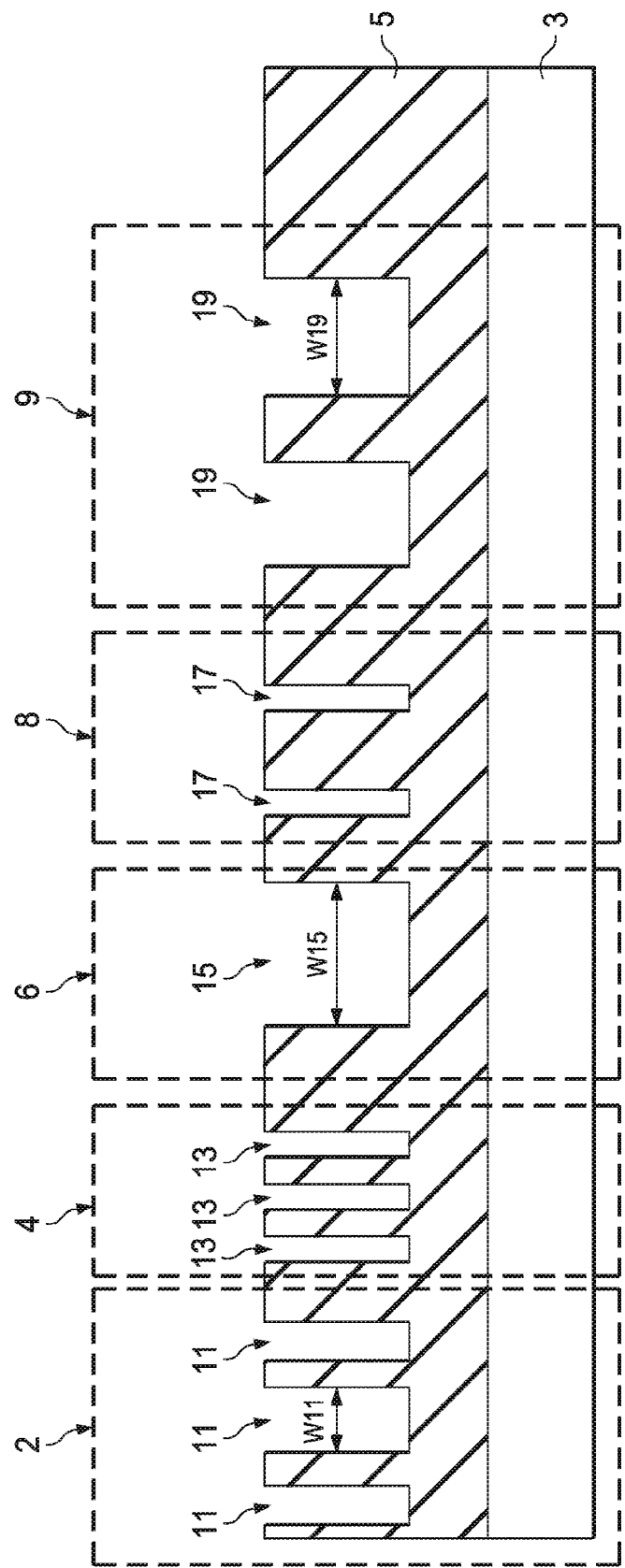
FIG. 2 depicts a cross-sectional view the semiconductor substrate of FIG. 1 following additional processing to form trenches for forming conductors using ECP, for use in illustrating the embodiments.

FIG. 2 depicts in a cross sectional view the patterned dielectric layer 5 over the substrate 3 of FIG. 1, after the etch process described above has been performed. FIG. 2 is simplified for explanation and it is to be understood that the device may include many levels of dielectric and metal layers included in the patterned dielectric layer 5 including gates, contacts, vias and other conductors, and that the substrate 3 may include active device regions such as source/drain regions formed as diffused portions of a substrate.

In FIG. 2, patterned areas 2, 4, 6, 8 and 9 are shown formed in the dielectric layer 5 after the etch step described above. In FIG. 2, each patterned area 2, 4, 6, 8 and 9 illustrates an example that has a different pattern density. Patterned area 2 illustrates an example where there is fairly high pattern density, that is, the conductor patterns fill most of the surface area in patterned area 2. In patterned area 2, several trenches 11 are formed which will be filled with conductor material in a subsequent ECP process, described below. Line width w11 (the widths of trenches 11 in patterned area 2) is relatively large, and the line spacing (the width of the dark areas in the dielectric material between trenches 11 in patterned area 2) is comparatively small with respect to the line width w11.

Patterned area 4 illustrates another pattern example. In patterned area 4, the line widths (the widths of trenches 13) are smaller than widths w11 for the trenches 11 in patterned area 2, and the trench widths for trenches 13 in patterned area 4 are about equal to the line spacing (the width of the dielectric layer 5 separating the trenches 13). Patterned area 6 illustrates an area with very high pattern density. In patterned area 6, there is one single very wide trench 15 with width w15. In this patterned area 6, almost all of the available surface area is covered by conductor material. Patterned area 8 illustrates a pattern of very fine conductor lines. Trenches 17 have relatively small width in the dielectric layer 5 and greater line spacing (the dielectric spacing between the trenches 17 is larger than in other patterned areas). Patterned area 9 illustrates trenches 19 with relatively large trench widths w19, and the trench spacing (dielectric layer 5 in patterned area 9 between trenches 19) is less than the trench width w19.

In forming conductors in the trenches 11, 13, 15, 17 and 19 in the patterned areas 2, 4, 6, 8 and 9 in FIG. 2, such as, for example, copper conductors formed by ECP, the photomask such as 22 used in FIG. 1 above will determine the trench pattern to be formed in the dielectric layer 5. A conductor pattern will then be formed as described below by using the ECP process to electroplate conductor material into the trenches 11, 13, 15, 17 and 19 in FIG. 2 to form the conductor lines of a metal layer. These steps will be performed for each layer of metal, metal 0, metal 1 etc. There may be 4, 5, 6, 7 or more layers of metal for an integrated circuit produced on a semiconductor substrate (for example, a semiconductor wafer) in some embodiments of an advanced semiconductor process. The ECP and CMP processes described herein are performed for each of these metal layers.

Figure 3A:
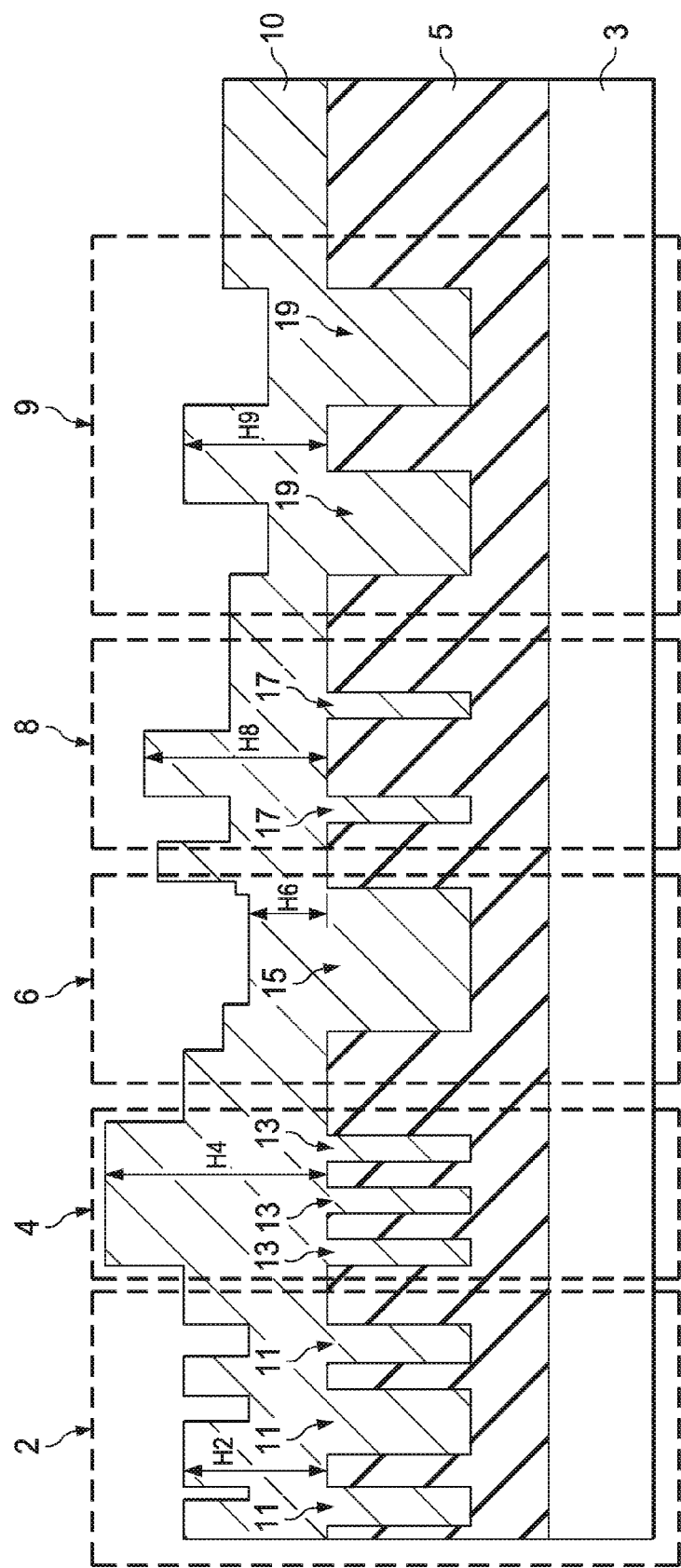
FIG. 3A depicts a cross-sectional view of the semiconductor substrate of FIG. 2 following additional processing using ECP, for use in illustrating the embodiments.

FIG. 3A illustrates substrate 3 and dielectric layer 5 of FIG. 2 in a cross-sectional view following an ECP process. Copper or other conductor material 10 is formed by electroplating and is shown filling the trenches 11, 13, 15, 17 and 19 in the patterned areas 2, 4, 6, 8 and 9 in the dielectric layer 5 respectively, and the conductor layer 10 is shown overfilling the trenches to cover the upper surface of dielectric 5. The material in copper layer 10 that overlies the upper surface of the dielectric layer 5 is the overburden.

As shown in FIG. 3A, the resulting thickness of the conductor 10 plated onto the substrate and the dielectric layer 5 varies in the different patterned areas 2, 4, 6, 8 and 9 with the height of the conductor 10 over the surface of the dielectric layer 5 shown as height H2, H4, H6, H8 and H9, respectively. As can be observed from the varying heights obtained for the conductor layer 10 after ECP, the height results obtained from the ECP process are affected by the differences in the trench patterns in the dielectric layer 5. At patterned area 2, the large line width and relatively fine space between the trenches results in peaks of a height H2 forming in layer 10. At patterned area 4, a higher hump of height H4 is seen where fine conductor trenches are filled with fine spacing between them. At patterned area 6, the height H6 of layer 10 is more uniform and lowered across patterned area 6 compared to patterned area 4. Layer 10 in patterned area 6 has a greater pattern density than in the other patterned areas. In patterned area 6, most of the available area s covered in conductor material, due to the use of a single wide trench filled with conductor. At patterned area 8, layer 10 shows peaks of height H8 where there is a relatively fine trench width with a larger spacing between the trenches. At patterned area 9, there is a peak of height H9 over the space between two wide trenches.

FIG. 3A illustrates that the line widths and line spacing of the conductor line patterns being formed by ECP in an area of the semiconductor substrate 3 affects the hump heights obtained during the ECP process, and thus the conductor line patterns being formed will affect the post ECP hump data map following the ECP process. Variations in the post-ECP hump height of conductor 10 are caused by the conductor patterns.

Figure 3B:
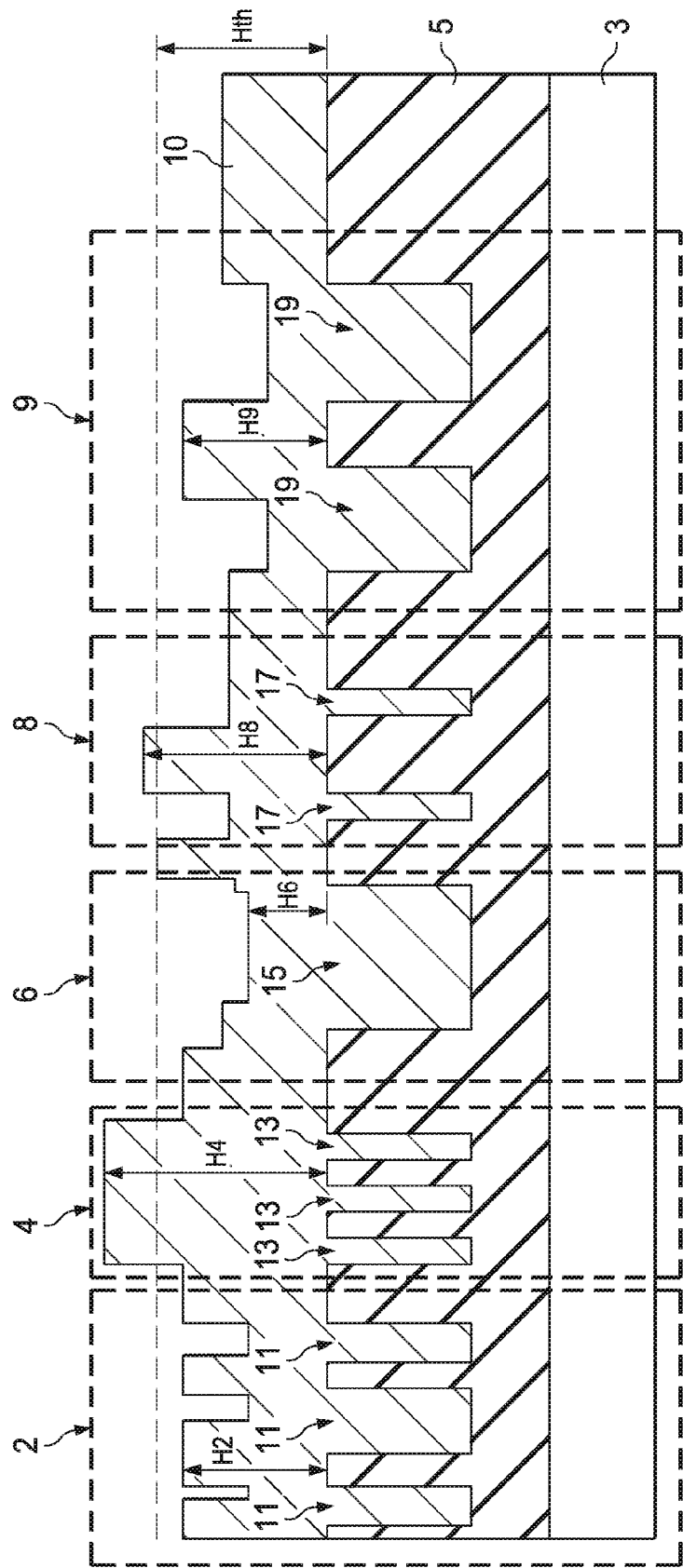
FIG. 3B depicts the cross-sectional view of the semiconductor substrate of FIG. 3A with a hump height threshold shown after ECP, for use in illustrating the embodiments.

FIG. 3B illustrates in a cross-section the post-ECP results of FIG. 3A, with a predetermined user defined hump height threshold Hth shown as a dashed line across the cross-section of each of the patterned areas 2, 4, 6, 8 and 9. As can be seen in FIG. 3B, there are some hump heights that exceed the threshold Hth. For example, H4 in patterned area 4 and H8 in patterned area 8 exceed the threshold Hth. In an embodiment method, described below, the threshold Hth is user selected, and patterned areas with hump heights greater than that threshold are identified as "hot spots".

After the ECP process is complete, a CMP process is performed on the conductor layer 10 to remove the portion of the layer 10 that is above the upper surface of the dielectric layer 5, the overburden portion. Post-CMP results obtained on ECP layers with large hump height variations, such as shown in FIGS. 3A and 3B are not uniformly planar. The CMP process used to polish the post-ECP layer 10 down to be co-planar with the upper surface of the dielectric layer 5 can result in problems, for example, when removing high humps in layer 10 in one patterned area, the CMP process may remove more of the layer 10 material than is desired, due to over-polishing of other patterned areas. Large metal pattern areas are sometimes polished below the desired co-planar surface of the dielectric layer and scoops or "dishing" can occur. This dishing problem is further accentuated when the dielectric layers used are "low-k" dielectric material which is relatively soft and more susceptible to over polishing.

By modifying the conductor line patterns for a metal layer to be formed by ECP (and CMP as described below), a more uniform conductor thickness can be obtained with lower variation in hump height. The hump height variations in a particular patterned area are determined by the current density during electroplating. If the current density during ECP is non-uniform across the semiconductor substrate, then non-uniform hump heights result. The conductor line patterns in the dielectric layer contribute to the non-uniformity in the current density during electroplating. By modifying the layout of the conductor line patterns, the current density during plating can be made more uniform and the post-ECP hump heights may also be made more uniform.

Figure 3C:
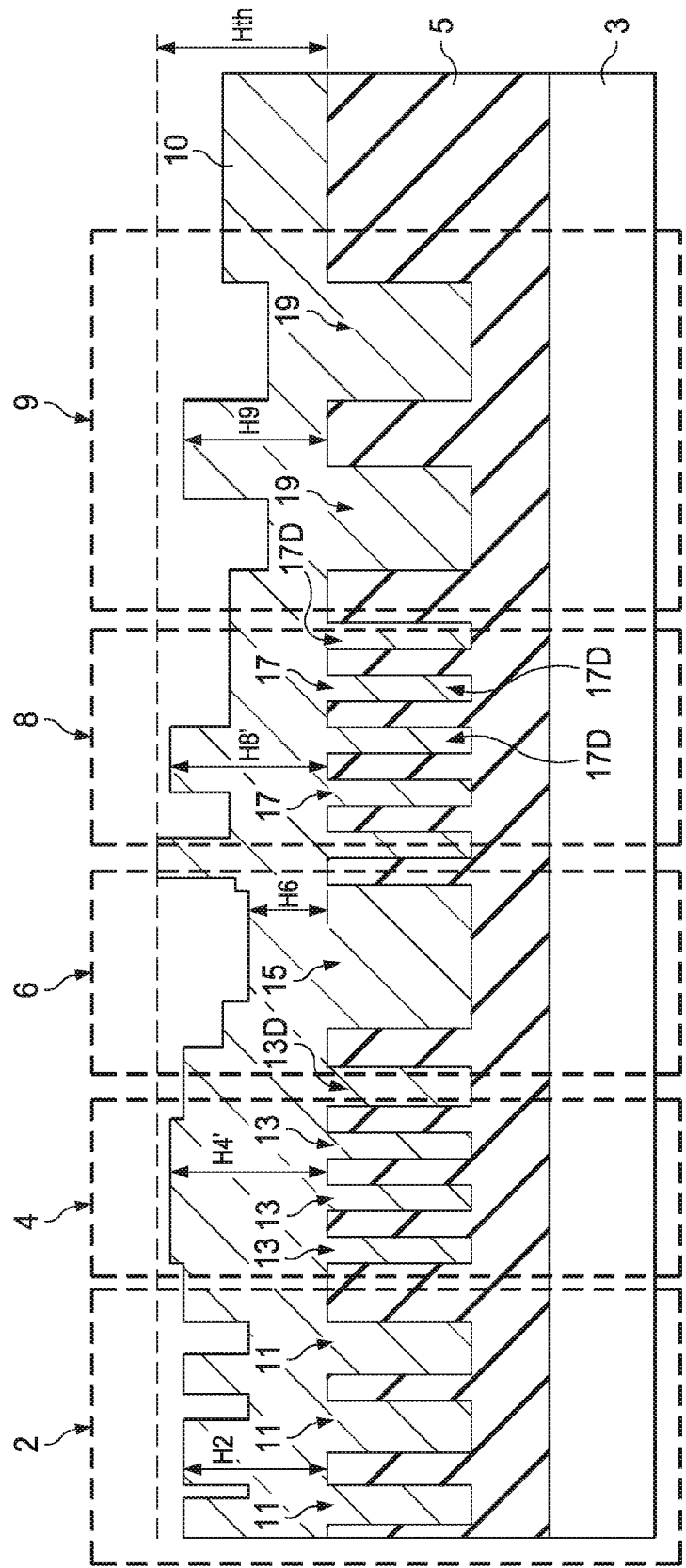
FIG. 3C depicts a cross-sectional view of the semiconductor substrate of FIG. 3B including dummy material formed by ECP, for use in illustrating the embodiments.

FIG. 3C illustrates in a cross-section the results of ECP after a modification to the patterned areas 4 and 8 of FIG. 3B by adding dummy conductor lines. In FIG. 3C, dummy trenches 13D and 17D are added to the patterned areas 4 and 8. The dummy conductor lines are added by modifying the layout for the selected metal layer. In FIG. 3C, the hump height H4' illustrates an improvement where the hump height in patterned area 4 after ECP is lowered by the use of the dummy trench 13D. Similarly, the hump height H8' in patterned area 8 illustrates an improvement in the hump height, a lowered hump height is achieved by the addition of dummy trenches 17D. The dummy conductors will not be connected electrically to circuit elements and are added to the layout to make the post-ECP hump heights more uniform.

Figure 4A:
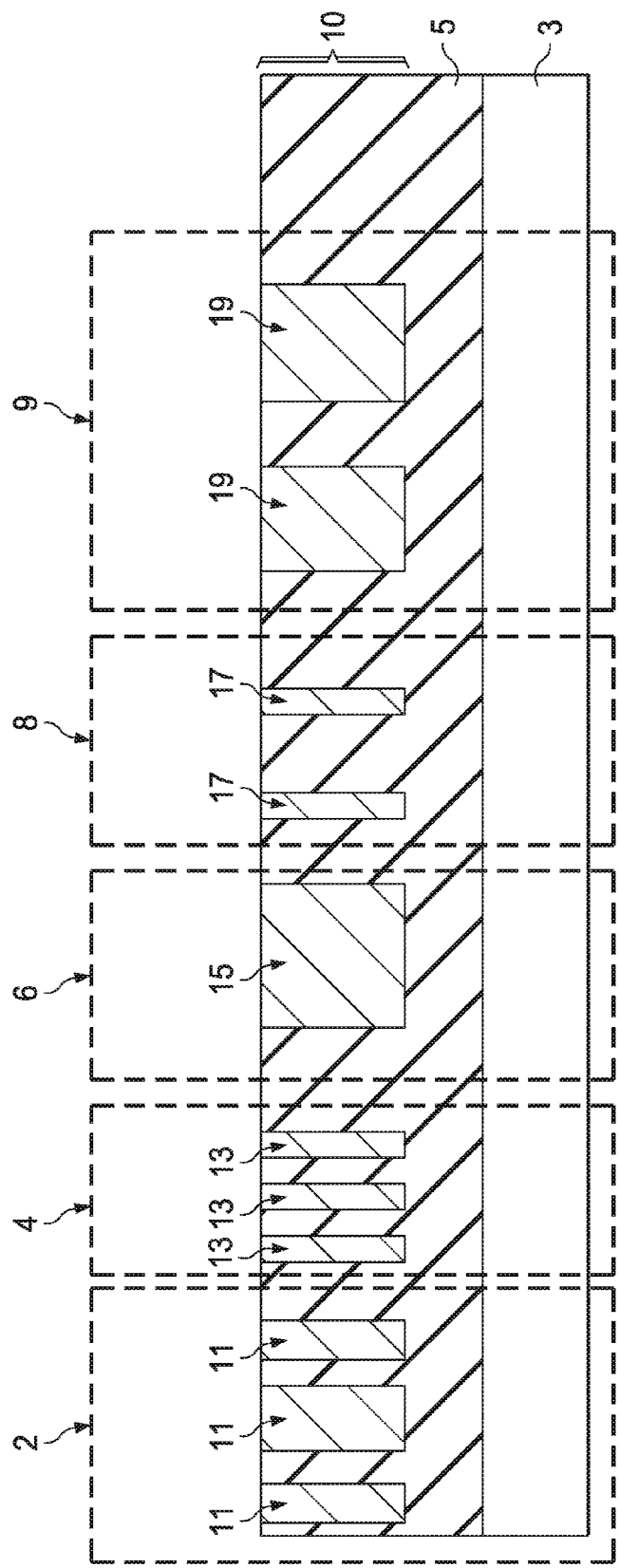
FIG. 4A depicts in a cross sectional view the semiconductor substrate of FIG. 3A following CMP processing in an ideal case, for use in illustrating the embodiments.

FIG. 4A illustrates a cross-sectional view of substrate 3 and dielectric layer 5 and conductor layer 10 after CMP. FIG. 4A is used to illustrate, for example, desired or ideal post-CMP results. In FIG. 4A, the CMP process has removed the overburden portion of layer 10, and the conductor lines can be seen in cross section as conductors in the trenches 11, 13, 15, 17 and 19 with an upper surface that is co-planar with the upper surface of dielectric layer 5. In an ideal case such as shown for explanation in FIG. 4A, the surface of the conductive material 10 in each trench post-CMP would be co-planar and uniform across the semiconductor substrate 3. In such a case the post-CMP hump data map would show no hump areas.

Figure 4B:
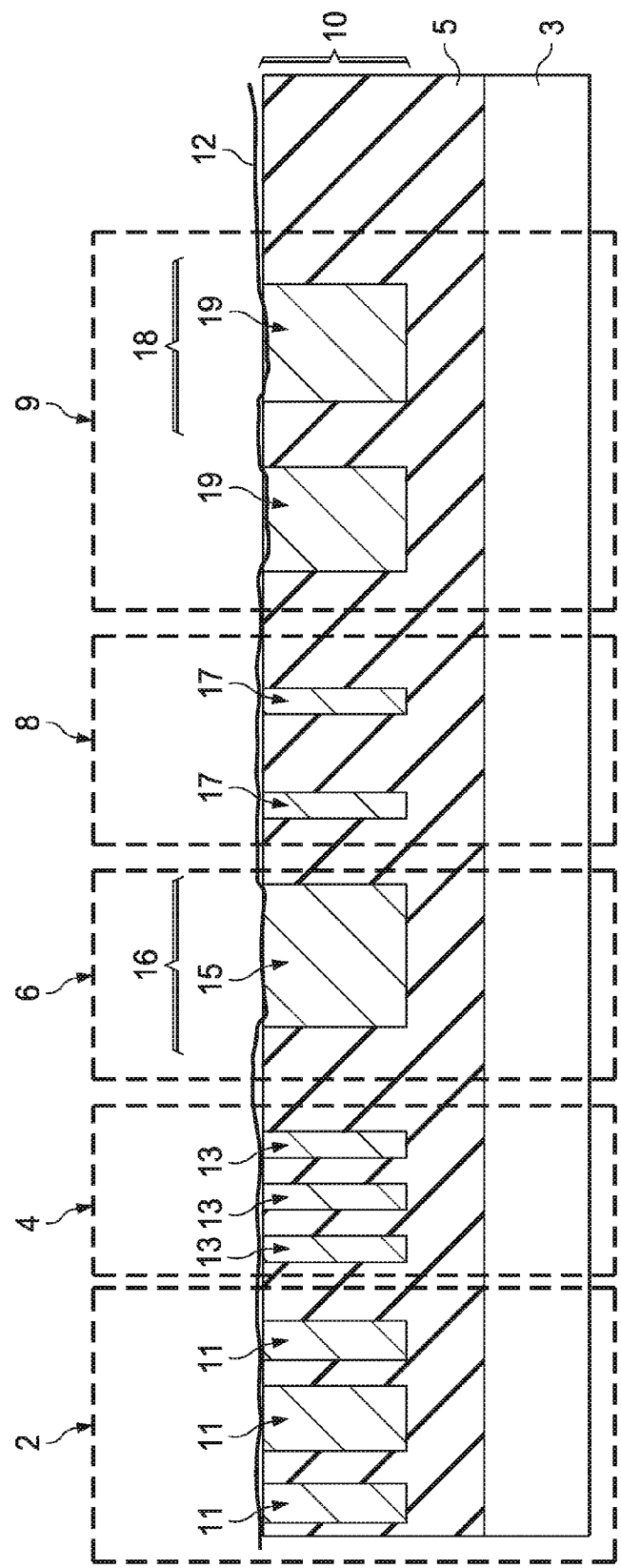
FIG. 4B depicts in a cross sectional view the semiconductor substrate of FIG. 3A following additional CMP processing, for use in illustrating the embodiments.

However, in a practical CMP process, the post-CMP results are not ideal. FIG. 4B depicts in a cross section an example of post-CMP results that are obtained from performing CMP on layer 10 formed over the dielectric layer 5 on substrate 3 shown in FIGS. 3A and 3B. Line 12 depicts a non-uniform polished surface that might occur when the CMP process is performed on layer 10 in FIG. 3, where the post-ECP hump height variation in layer 10 in the different patterned areas is significant. Areas 16 and 18 illustrate the "dishing" effect that can occur when the CMP process removes too much of the conductive material 10 in certain areas.

Figure 4C:
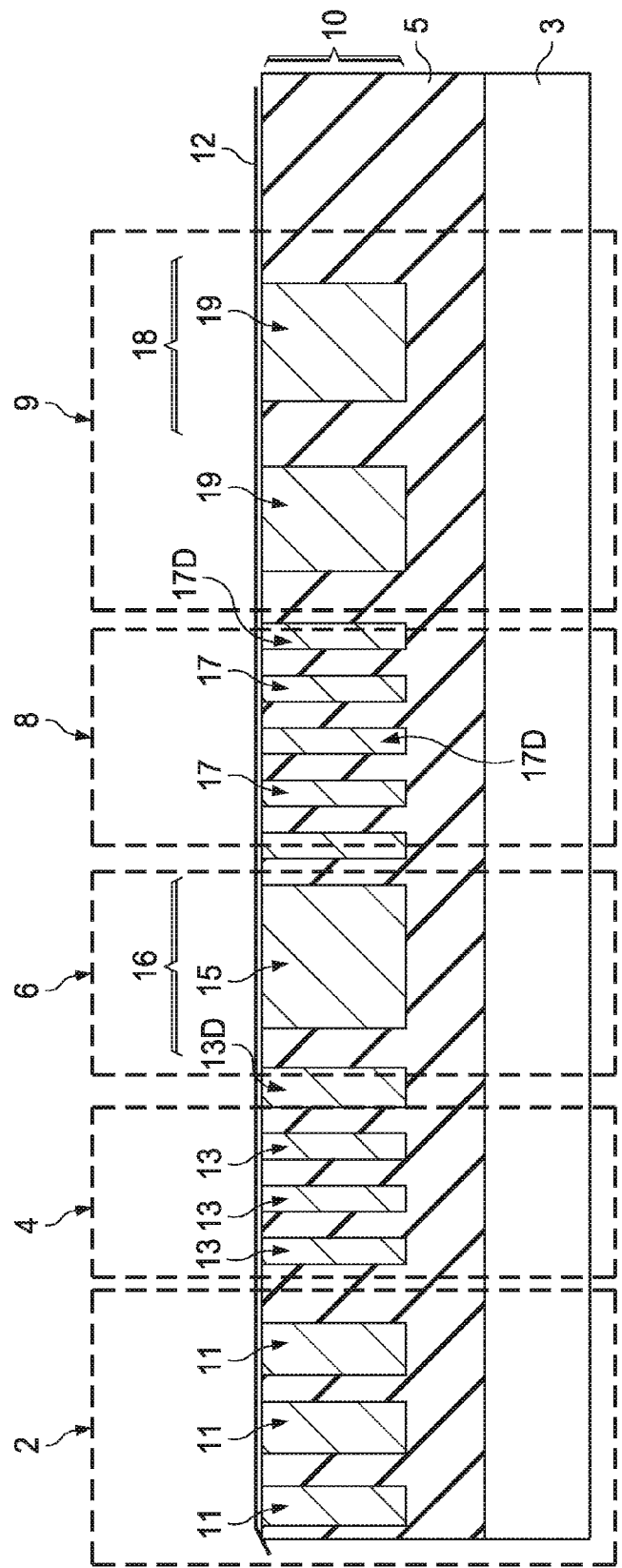
FIG. 4C depicts in a cross sectional view the semiconductor substrate of FIG. 3C following additional CMP processing for use in illustrating the embodiments.

An improved post-ECP result (lower hump height variations) also improves the post-CMP result. FIG. 4C illustrates in cross section a post-CMP result for the improved post-ECP results of FIG. 3C. In FIG. 4C, the line 12 that illustrates the polished surface after ECP shows an almost planar surface on dielectric layer 5. By modifying the layout and adding dummy conductor trenches to the patterned areas 4 and 8 in FIG. 3C, the post-ECP results were improved. The CMP process then also improves, because a more uniform conductor layer with less variation in hump heights is easier to process using CMP to obtain a planar surface. In FIG. 4C, the expected surface shown by line 12 is closer to the ideal case of FIG. 4A, and the dishing effects in areas 16 and 18 of FIG. 4B are reduced.

Since modifying the conductor layout can improve results of post-ECP and post-CMP processes, modifications to improve uniformity in ECP such as adding dummy conductors to the patterns for a metal level are used in prior approaches. However, in the prior approaches, verifying that the modification to the layout actually improved the ECP and CMP results required manufacturing a modified photomask for the conductive line pattern, such as a modified photomask 22 in FIG. 1, and then, making additional test wafers. This iterative photomask manufacturing and test wafer process is time consuming and expensive. It is desirable to simulate the ECP and CMP results obtained from the process and to use the simulator results to verify that the proposed layout pattern for a metal layer returns acceptable post-ECP and post-CMP results prior to any manufacture of the photomasks. However, the ECP and CMP simulations in the prior approaches were not sufficiently accurate, and the simulator output results did not match the results of the ECP processes; so it was not feasible to use these simulators to optimize the layouts before making the photomasks.

In the prior art ECP simulations, only layout effect factors were used with the ECP simulators to determine the predicted post-ECP results. In the prior approach, for each of many unit grid areas for a metal layer on a semiconductor wafer, the line width and line spacing was used, with the ECP simulator, to predict the post-ECP hump heights. The ECP simulator is calibrated to a known process and to a known plating tool, and using the line width and line spacing, for each unit grid area, a resulting post-ECP thickness was predicted using a software model for the plating process. However, the predicted post-ECP results obtained did not track the results obtained from the actual process on the wafers, and so the predicted post-ECP hump heights obtained were not useful.

It has been observed that each of three factors, Factor 1, Factor 2 and Factor 3, in the metal conductor patterns actually affects the hump heights seen in post-ECP results in experimental wafers. In some embodiments of the present disclosure, each of the three factors is determined for a proposed layout for a selected metal layer. V-ECP and V-CMP simulators are used, with each of the three factors as inputs to the simulators, to provide predicted post-ECP and post-CMP hump height data maps for the proposed layout. In various embodiments, modifications are made to the proposed layout, or in alternative embodiments, to the process recipes, and additional simulations are performed. When a simulator result is obtained with acceptable hump height uniformity, the modified layout is used to generate a photomask generation file, and a photomask is manufactured. The use of all three of the factors increases the accuracy of the ECP simulation, and also the CMP simulation, so that the predicted hump data map tracks experimental wafer results very closely. With the use of some embodiments, a proposed layout modification can be verified and there is no need to modify and manufacture multiple versions of the photomasks.

In some embodiments, the three factors are determined for the conductor line pattern for a particular metal layer in a unit grid area, a global effects factor (Factor 1), a local effects factor (Factor 2) and a layout effects factor (Factor 3). Factor 3 is similar to the layout effects used in prior approaches. By using all the three factors Factor 1, Factor 2 and Factor 3 calculated from a proposed pattern for a given metal layer, and by inputting the data for all three factors into a V-ECP simulator, an accurate predicted post-ECP hump data map is obtained. This predicted post-ECP hump data map predicts the post-ECP results for the proposed design, and it is then produced on an actual wafer. The predicted post-ECP hump data map is used to identify "hot spots" such as those shown in FIG. 3B. The proposed layout of the metal layer may then be modified, and the modified layout is used with the three factors in the ECP simulator to verify whether the "hot spots" are removed by the modifications. In this manner, the proposed layout is optimized for ECP and CMP processing.

For example, in FIG. 3B, patterned areas 4 and 8 have greater hump height than the surrounding areas and are shown as "hot spots," where hump heights exceed a threshold Hth. In FIG. 4B, post-CMP results show dishing problems and the non-planar surface that may result when CMP is performed on a conductive layer 10 with these post-ECP "hot spots." In some embodiments, these "hot spots" are reduced or eliminated before a wafer is processed in ECP and CMP tools.

Changes to the proposed IC layout are made, and an iterative approach can be used with the V-ECP simulator to verify that the modified layout will have fewer "hot spots." In an embodiment, additional dummy conductor pattern areas are added to a proposed layout pattern, for example. The addition of dummy pattern areas can increase the pattern uniformity and reduce the hump height in the "hot spots" as shown in FIG. 3C. Conductors in the proposed layout can be rerouted or widened, for example, to change the conductor pattern density in certain areas of the substrate where the simulators indicate "hot spots" may occur.

In some embodiments, after a change is made to the conductor pattern, the V-ECP simulator can be used again, with the updated data for each of the three factors, to verify that the changes made have improved the hump data map (reduced the number of "hot spots"). By using the V-ECP and V-CMP simulators and by optimizing the conductor pattern prior to the manufacture of photomasks, the need for subsequently modifying photomasks to address ECP hot spots is eliminated, design time is saved, and manufacturing costs are reduced by use of various embodiments of the present disclosure.

The three factors are now further described. It has been observed that the global conductor pattern effects impact the post-ECP hump data obtained for a particular pattern. That is, the pattern density for a conductor line pattern for an entire wafer, and the overall surface coverage of the plated conductor over the entire wafer surface area, impacts the post-ECP hump height variations. This factor, Factor 1, is the global effects factor. In some embodiments, this factor is obtained by calculating the surface area of the substrate covered by conductor material for the selected metal layer, over the total surface area of the substrate. Factor 1 is then stored as input data for use in the V-ECP simulation for each unit grid area.

It has also been observed that local effects or environmental effects affect the post-ECP results. For experimental wafers, the post-ECP data maps are examined in cases where similar patterned areas are formed that are located in different parts of a wafer, or different areas within an integrated circuit die on a wafer. For example, the conductor line trenches in patterned area 2 of FIGS. 3A and 3B might be formed in two different areas of an integrated circuit die. In one area of the integrated circuit die, the conductor line trenches of patterned area 2 were adjacent additional conductor patterns, such as shown in FIGS. 3A and 3B, where patterned area 4 has a different conductor pattern formed very close to patterned area 2. In the experimental wafers, when the second area is examined, the same pattern (such as, for example, patterned area 2 in FIGS. 3A, 3B) was formed in an area of the integrated circuit where there are no other adjacent metal patterns. Using hump data maps from the experimental wafers, it is observed that even when the same conductor line pattern (for example, patterned area 2 of FIGS. 3A, 3B) is formed in two different regions of a substrate, different post-ECP hump height data are observed for the two (otherwise identical) conductor line patterns. This difference in the hump height data map is due to local pattern effects in the area surrounding the conductor pattern. The surrounding conductor patterns impact the hump height data from the ECP and CMP processes.

In some embodiments, Factor 2, the local effects factor, addresses these effects. To determine Factor 2, a calculation is done by dividing the entire substrate area into unit grid areas. As described below, each unit grid area has a Factor 3, the layout effects factor, associated with it. Each unit grid area is selected to be 10 microns by 10 microns, for a non-limiting example. To determine Factor 2 for each unit grid area, a larger local grid area is associated with each unit grid area. The local grid area is approximately centered on the unit grid area. Factor 2 is calculated for each of these local grid areas. This calculation is made by finding the surface area that is covered in the conductive material over the total surface area for each local grid area, that is, the pattern density is determined for the local grid area. In an example embodiment, a local area of 100 microns×100 microns was used, although larger or smaller local grid areas could be used as well. The area of the local gird area covered by the conductor pattern over the total available surface area provides Factor 2 as a pattern density for the local grid area. In some embodiments, Factor 2 is calculated and stored for each unit grid area for the entire wafer. The Factor 2 data is then later retrieved for use in a V-ECP simulation.

In some embodiments, Factor 3 is the layout effects factor. Factor 3 is determined for each of the unit grid areas. Layout effects are those effects determined by each individual line or pattern to be plated in ECP. For example, in FIGS. 3A and 3B, patterned areas 2, 4, 6, 8 and 9 each have one or more trenches to be filled with conductor layer 10, as described above. Each of the trenches forms a conductor line pattern. The width and spacing of the conductor line patterns in each of the unit grid areas affects the hump heights obtained in the ECP process.

Figure 5:
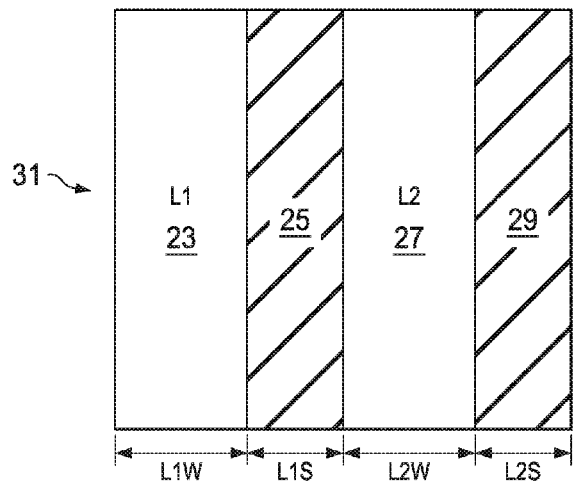
FIG. 5 depicts in a plan view an example conductor line pattern for a unit grid area for use with the embodiments.

FIG. 5 illustrates a pattern in a grid area 31, in a plan view. In FIG. 5, a conductor line pattern L1 is formed and spaced from a parallel conductor line pattern L2. The conductor line patterns L1 and L2 are trenches 23 and 29, and in cross section would appear like trenches 11 in FIG. 2, for example. Dielectric spacing material 25 and 29 electrically isolates the conductor line patterns. The grid area 31 is a small portion of a semiconductor wafer, 10×10 ums, or 20×20 ums, or a similar grid size, for example.

In one embodiment, Factor 3 is measured as a line edge density (LED) for each unit grid area over the semiconductor wafer. In this embodiment, the LED is calculated as LED=1/(line width+line spacing), and may have units such as $microns^{-1}$. For example, if a line was 100 nanometers in width and it had a line spacer that was 100 nanometers, the LED for this pattern would be 1/0.2=5 $microns^{-1}$. In the example shown in FIG. 5, if the width L1w=125 nanometers, and the spacing L1s=125 nanometers, and likewise the width L2w=125 nanometers and the spacing L2s=125 nanometers, then the LED=1/(0.125+0.125+0.125+0.125)=1/0.5=2 $microns^{-1}$.

In another alternative embodiment, pattern density is used for Factor 3 for each unit grid area. In FIG. 5, the pattern density for unit grid area 21 would 50% or 0.5, because half of the available area is covered by the conductor pattern of lines L1 and L2. Note that the pattern density can also be determined by converting the LED, by multiplying the LED for each line by the line depth to determine the surface area covered by conductors, out of the total available surface area, in the grid area.

In some embodiments, Factor 3 is determined for each unit grid area. The entire wafer is broken into minimum unit grid areas, for example, in one embodiment grid sizes of 20 microns×20 microns is selected. In another alternative embodiment, 10 microns×10 microns is selected as a unit grid area.

In contrast to the existing approaches, in various embodiments of the present disclosure the three factors Factor 1, Factor 2 and Factor 3 are all used together, in some embodiments, with a V-ECP simulator. It has been observed that by using all three factors in a V-ECP simulator, the embodiments provide a V-ECP simulation that outputs a predicted post-ECP "hump data" map. This predicted post-ECP hump data map has been found to be matched to post-ECP hump data obtained from test wafers. In additional embodiments, the V-ECP simulations use at least one of Factor 1, and Factor 2, along with Factor 3, to perform a more accurate V-ECP simulation when compared to the prior approaches. By adding the additional factor or factors (Factor 1, Factor 2, or both) to the layout effects factor, Factor 3, in the simulation input, the accuracy of the predicted post-ECP output is greatly increased.

In some embodiments, the V-ECP simulator is a software program that simulates the results from the electroplating process. The V-ECP simulator is calibrated to the particular ECP equipment being used and to the semiconductor process being used. Different predetermined ECP recipes that are available are characterized and stored as options for the user to select, so that the varying results are easily compared when using the different ECP recipes. For example, in various embodiments, the ECP recipes vary wafer rotation speed, plating time, temperature, voltage/current applied during plating, the plating solution selected, etc. and these recipes are stored as part of the input data used by the V-ECP simulator.

In one embodiment, the ECP simulator is implemented as a correlated data look-up table formed using experimental data from test wafers. In this approach, each of the three factors Factor 1, Factor 2 and Factor 3, are determined and presented as inputs to the V-ECP simulator for each unit grid area. The three factors, plus the process equipment details and user selected process recipes, are input into a table that is built from experimental wafer runs using the same process equipment and the same ECP recipes on previously processed wafers. By using the correlated data lookup table, a predicted hump height for the ECP process is obtained for each unit grid area. This predicted post ECP hump height is used, with all of the other predicted hump heights for the entire wafer, to form a predicted post-ECP hump height map for the entire semiconductor wafer. In some embodiments, this correlated data lookup table provides a virtual ECP simulation that is very accurate and is fast, in terms of processing time, to execute.

In an alternative embodiment, a computer software modeling approach is used to create the V-ECP simulator. In this embodiment, software is used to model, using algorithms, the ECP process to form an executable simulator. For a proposed layout of a metal layer, the three factors are determined for each unit grid area, and input to the executable simulator, which is calibrated to a particular semiconductor process and user selected process recipes.

In either of the above described simulator embodiments, the V-ECP simulator includes at least one of the factors Factor 1, Factor 2, and also Factor 3, as inputs, in contrast to the prior ECP simulators. The predicted ECP result tracks the results obtained on wafers in the process. The post-ECP conductor thickness predicted by the simulator takes at least one of Factor 1, Factor 2 and Factor 3 into account for each unit grid area on the entire wafer. The predicted post-ECP hump height data that is output by the V-ECP simulators of the embodiments has proved to be very closely matched to test wafer results. Some embodiments are used to identify "hot spots" as shown in FIG. 3B above, and provide the ability to modify the layout for a metal layer, as shown in FIG. 3C above, and then use the V-ECP simulator to verify that improved post ECP results that are obtained.

Figure 6:
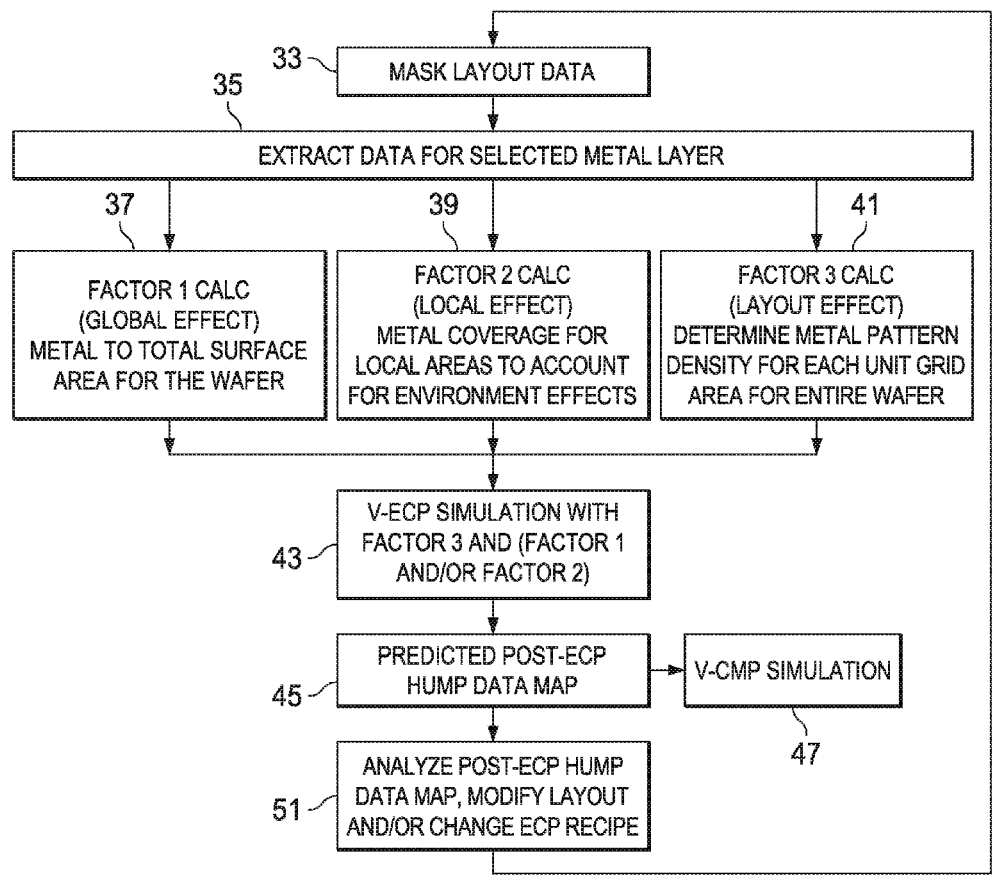
FIG. 6 depicts in a flow diagram an example embodiment using a V-ECP simulator.

FIG. 6 illustrates, in a flow diagram view, a first illustrative method embodiment for using a V-ECP simulator with Factor 1, Factor 2 and Factor 3 described above. The method is implemented using a computing device having executable programs and data stored in non-transitory computer memory devices such as hard disk drives, CD/DVD disks, FLASH memories, and the like. Servers or network data storage may be used. In various embodiments, application programs are written and stored in executable form, and executable code may be retrieved from the memory by a processor, and the instructions in the software may be executed by the processor during the performance of the method steps.

In the embodiment of FIG. 6 the method begins at step 33, when mask layout data is received. The mask layout data, for a non-limiting example, is provided in GDSII format, although other formats of graphical design data for integrated circuits could be used. The mask layout data received in the GDSII file in step 33 includes layout data for the metal layers in the design. At step 35, the data needed for the V-ECP and V-CMP simulations for a selected metal layer are extracted from the GDSII data. For example, if the metal layer to be evaluated is metal-1, then the mask layout data corresponding to the conductor line patterns for metal-1 are extracted. The data extraction of step 35 is done to reduce the amount of data being stored and retrieved for the V-ECP simulation. The V-ECP simulation will be performed for each of the selected metal layers, so in step 35 the layout data needed for any given metal layer is extracted for use in the method, and this extraction step is repeated later for the remaining layers. For example, if the selected layer is metal 1, then the layout data corresponding to the metal 1 pattern is extracted from the GDSII data file.

At step 37, Factor 1, is determined. As described above, Factor 1 is calculated from the total pattern area as a percentage or ratio of the conductor material surface area for the selected metal pattern to the total surface area of the semiconductor wafer to be plated, and Factor 1 measures the global pattern density of the conductor material over the wafer. Factor 1 will be used by the ECP simulator to in some embodiments refine the post-ECP prediction for the hump height that will occur for each unit grid area.

At step 39 in FIG. 6, Factor 2 is determined for each unit grid area over the semiconductor wafer. As described above, the wafer is partitioned into local area grids or tiles, and these may overlap. For example, grids of 100 micron×100 micron, or smaller or larger areas could be used. Each local grid area corresponds to an area surrounding and approximately centered on a particular unit grid area. The local grid area could correspond to a single integrated circuit die area, in some example embodiments. For example, this local area might be a 10000 square micron area, (100 ums×100 ums) or some other selected area. The Factor 2 calculation described above is made and the Factor 2 data is stored for the local effects factor for each of the unit grid areas for the entire wafer. Factor 2 for each unit grid area is used in some embodiments in the ECP simulation to refine the prediction the simulator makes for the post-ECP hump height of the conductor material in the unit grid area.

After the data for the selected metal layer is extracted, the layout effects data factor, at step 41, Factor 3, is calculated for each of the unit grid areas over the entire wafer. As described above Factor 3 is an LED calculation, in an embodiment. In an alternative embodiment, Factor 3 is a pattern density calculation for the unit grid area. There are hundreds or thousands of these unit grid areas for the semiconductor wafer. For each unit grid area on the semiconductor wafer the Factor 3 results are stored, in a non-transitory memory or computer readable medium. In some embodiments, a form of storage for the Factor 3 data is a map file with the unit grid areas indexed by their physical X, Y location on the wafer, for example.

As shown in FIG. 6, in this embodiment the calculation of the three factors Factor 1, Factor 2 and Factor 3, is performed in parallel (steps 37, 39 and 41, respectively). In various alternative embodiments, these three factor calculations (many calculations are performed over the entire wafer) are done in any order and in an example, are done serially, as is convenient in a given application. Additional modifications to the order of steps are contemplated and form additional alternative embodiments that are within the scope of the appended claims.

At step 43, the V-ECP simulator is executed using at least one of the factors Factor 1 and Factor 2, and either one or both of these factors are used along with the Factor 3 data from steps 37, 39 and 41 as data inputs. In an embodiment, all three factors are used in the simulations. In other embodiments, at least one of Factor 1, and Factor 2, are used in a simulation along with Factor 3 (the layout factor). As described above, in one example embodiment, the V-ECP simulator is implemented as a calibrated look-up correlation table, where the predicted post-ECP hump heights are stored in a look up table, using experimental data from previous wafer runs. At step 43, the V-ECP simulation is performed using an ECP model that is calibrated to the particular semiconductor process that will be used to perform the ECP process on the wafers. The V-ECP simulator is calibrated using prior results from test wafers, or from prior production wafers, as metrics, for example. Due to the use of at least one of Factor 1 and Factor 2, along with Factor 3 for the unit grid areas during the V-ECP simulation, the predicted post-ECP hump data map is accurate. In some embodiments all three factors, Factor 1, Factor 2 and Factor 3 are used. Further, the predicted post-ECP hump heights from the V-ECP simulator at step 43 match the hump heights that are obtained in actual wafer runs using the corresponding ECP tools and recipes.

At step 45, a predicted post-ECP hump data map is output from the V-ECP simulator, which contains an entry for each unit grid area on the semiconductor wafer representing the predicted post-ECP metal conductor thickness for the unit grid area. The post-ECP hump data map output by the V-ECP simulator is stored for later retrieval in a computer memory in non-transitory form. In some embodiments, the predicted post-ECP hump data map is displayed for visual inspection as a two dimensional image of the wafer on a graphical computer display, for example, in one embodiment the predicted post-ECP data map is presented as a visual representation of the predicted hump height patterns in the conductor layer after ECP. The graphical display is convenient for human operators to visually inspect. In an example embodiment, colors were used to indicate higher humps and visually represent "hot spots" hump heights that exceed some predetermined threshold, as shown as Hth in FIG. 3B, for example.

At step 51, the predicted post-ECP hump data map is analyzed. If hump heights in the predicted post-ECP hump data map exceed certain predetermined acceptable hump height thresholds, these are identified as "hot spots," as illustrated in FIG. 3B above. For example, returning to FIGS. 3A, 3B above, the patterned areas 4 and 8 have hump heights H4 and H8. If as shown in FIG. 3B, a hump height threshold Hth was defined near the height H2 of patterned area 2, then patterned areas 4 and 8 have hump heights in the predicted post-ECP hump data map that exceed that threshold; and patterned areas 4 and 8 would be marked as "hot spots".

Continuing at step 51, if the predicted post-ECP hump data map has "hot spots," the mask layout for the selected metal layer is modified to improve the ECP results. For example, the metal conductors for the selected metal layer could be routed to different areas; alternatively the metal conductor line widths and line spacing could be changed to be larger or smaller. Also, as described for FIGS. 3C and 4C above, dummy metal conductor areas are added to the conductor line pattern in the "hot spots" to improve the conductor line pattern uniformity. Increased conductor line pattern uniformity improves plating uniformity in the ECP process and this reduces hump height variations in the post-ECP thickness of the plated metal conductor, as described above with respect to FIG. 3C.

After the proposed layout is modified, at step 51, in one embodiment, the method in FIG. 6 is iteratively performed. Using the modified layout and starting again at step 33, the V-ECP simulator at step 43 is used to verify that the post-ECP hump data map of the modified layout for the selected metal layer is improved, and that the hump heights in the predicted post-ECP hump data map at step 45 are reduced to allowable levels. In one embodiment, this iterative method continues until acceptable post-ECP hump heights (less than a predetermined hump height threshold) are achieved for each unit grid area across the wafer. In other embodiments, the iterative method is repeated a selected number of times, as determined by the user. In still other embodiments, the iterative method is repeated until the predicted post-ECP hump height data map does not further improve.

The V-CMP simulator at step 47 simulates a chemical mechanical polishing process on a wafer for a given CMP tool with a particular semiconductor process. Like the V-ECP simulator, the V-CMP simulator is calibrated to a particular piece of CMP equipment and to the particular semiconductor process. In CMP, a chemical slurry is dispensed onto a rotating abrasive polishing pad that is mechanically pressured against the surface of a dielectric layer or wafer that is being reduced or smoothed by polishing. The V-CMP simulator thus takes into account the type of slurry, the type of pad, the speed of rotation, the pressure applied, and the position of the polishing pad which moves on an arm. The V-CMP simulator at step 47 may also include a selection of predetermined CMP recipes where the user can select. The recipes include type of slurry used, slurry pH, pad pressure, pad type, processing time, and other variables are sometimes varied.

In one embodiment, the V-CMP simulator at step 47 is also implemented as a correlated data look up table, similar to the V-ECP simulator described above. The CMP process recipes are stored with results taken from test wafer runs to form the correlated data look-up table. Further, because the predicted post-ECP hump data map from the V-ECP simulation at step 45 now closely matches the actual wafers processed when using the various embodiments described above, a highly accurate V-CMP simulation is performed, and thus, an accurate predicted post-CMP hump data map obtained. This post-CMP hump data map is also used to further spot potential "hot spots" on the substrate after the CMP process. A user provided post-CMP hump height threshold can be compared to the post-CMP hump height data map, and areas where the V-CMP simulator predicts the post-CMP hump height exceeds the threshold can be identified as "hot spots", similar to the threshold comparison in FIG. 3B above. These "hot spots" may include areas of "dishing" where the dielectric material is removed during CMP, for example as shown in FIG. 4B. The proposed layout for the design can then be modified and further optimized for the CMP process to obtain an improved post-CMP result, such as shown in FIG. 4C. All of the modifications described above to the proposed layout are made prior to the photomask manufacturing steps, further increasing wafer yield and, without the need for repeated photomask manufacturing steps, and without making test wafers.

The method embodiment of FIG. 6, and the alternatives described below, is performed for at least one metal layer and up to each metal layer used in an integrated circuit design to be implemented on a semiconductor wafer. Thus, the photomasks such as 22 in FIG. 1 that determine the metal conductor pattern for each metal layer to be formed using an ECP process in a multilayer design are optimized for ECP and CMP processes. The layout is optimized prior to the manufacture of the photomasks by use of various embodiments. When the photomasks are finally manufactured, the hump height variation results from the ECP process and the CMP process for each metal layer on the wafers manufactured using the photomasks will be within predetermined threshold limits, because the layout design has already been optimized by use of the V-ECP and V-CMP simulators of various embodiments before the photomask manufacturing step.

In alternative embodiments, the V-ECP simulator further provides a way to optimize the selection of an optimal ECP recipe among known ECP recipes for the particular ECP tools to be used in production. This is also described at step 51 of FIG. 6. The ECP recipe selected is modified and the V-ECP simulation at step 43 of FIG. 6 is again performed to determine if better post-ECP results (e.g., no or fewer hot spots in the predicted post-ECP hump data map) are obtained. In this embodiment, the post-ECP results are improved without the need for modifying the layout design. In another alternative method embodiment, both the layout and the ECP recipe are modified, and the V-ECP simulation again performed, to obtain optimal results.

Figure 7:
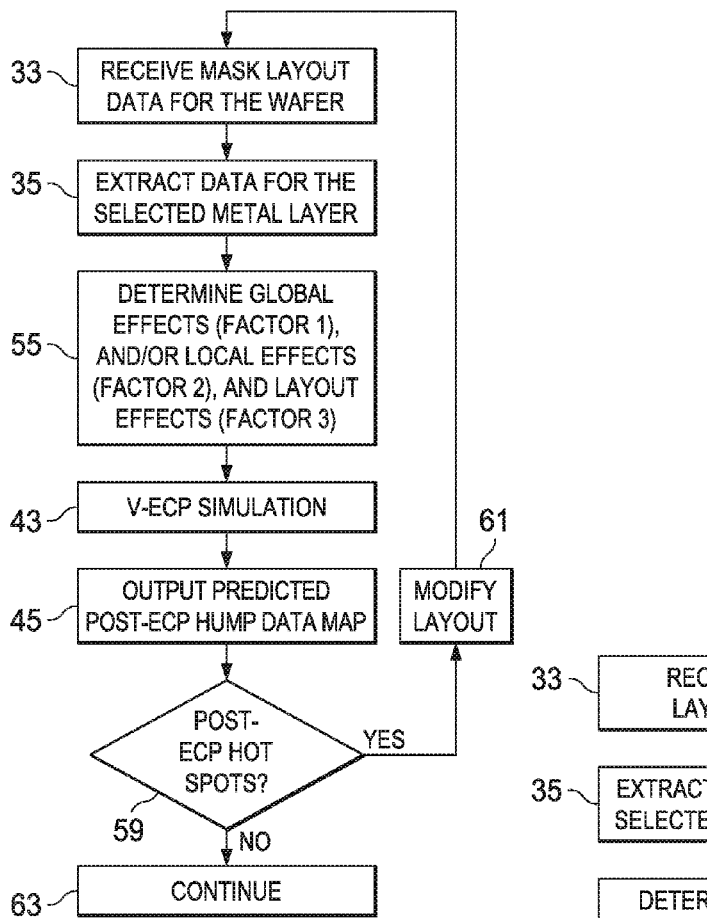
FIG. 7 depicts in a flow diagram an example method embodiment using an iterative method with a V-ECP simulator.

FIG. 7 depicts in a flow diagram an alternative method embodiment showing an iterative approach for modifying the layout to obtain acceptable ECP results. Some steps of this method embodiment of FIG. 7 are common to the above described method of FIG. 6, and like reference numerals are used for like steps. For example, the method of FIG. 7 also begins at step 33 as described above. Mask layout data such as GDSII formatted data is received for a conductor pattern for a proposed IC to be produced on a semiconductor wafer using ECP/CMP processes. At step 35, the needed data is obtained for the selected metal layer. At step 55, the three factors Factor 1, 2 and 3 are determined for each unit grid area over the entire wafer, as described above. In an embodiment, at least one of Factor 1, and Factor 2, are determined for each unit grid area for the entire wafer, and these are used along with Factor 3 in the V-ECP simulations. In one embodiment, all three factors Factor 1, Factor 2 and Factor 3 are used in the V-ECP simulations. For simplicity in illustration the steps 37, 39 and 41 of FIG. 6 above are not again described in detail here, but are instead shown here as a single, combined step 55. At step 43, the V-ECP simulator is again executed. A predicted post-ECP hump data map is output at step 45. At step 59, a comparison is made for each pattern in the post-ECP hump data map to a predetermined hump height threshold, and hot spots in the post-ECP hump data map are identified, as shown in FIG. 3B above.

If any hot spots are identified at step 59, then at step 61, the pattern layout for the particular metal layer is modified, for example, by rearranging the conductor pattern for the particular metal layer, or by adding dummy conductor patterns to increase pattern density uniformity for the particular metal layer as described with respect to FIG. 3C. The entire process of FIG. 7 is then repeated from step 33. The method embodiment of FIG. 7 is continued iteratively until the comparison at step 59 is negative, that is, until no post-ECP hot spots are found in the comparison at step 59. The method then continues to step 63. Alternatively, the method of FIG. 7 may end when the improvements that occur in the post-ECP hump height data map at step 45 between successive iterations are less than some predetermined percentage; indicating little further improvement is made between iterations.

In an embodiment, the method of FIG. 7 is performed for each metal layer in an IC design, as each metal layer is formed using ECP and CMP processes. Alternative embodiments include performing the method of FIG. 7 on 1, 2 or more metal layers.

At step 63, the method continues. The output of the V-ECP simulation can be used as the input to a V-CMP simulation as in FIG. 6 above, or the photomask generation (PG) data could be output at this step. Photomask generation (PG) data files are output to a photomask manufacturing facility that makes the reticle corresponding to the pattern, such as photomask 22 in FIG. 1.

Figure 8:
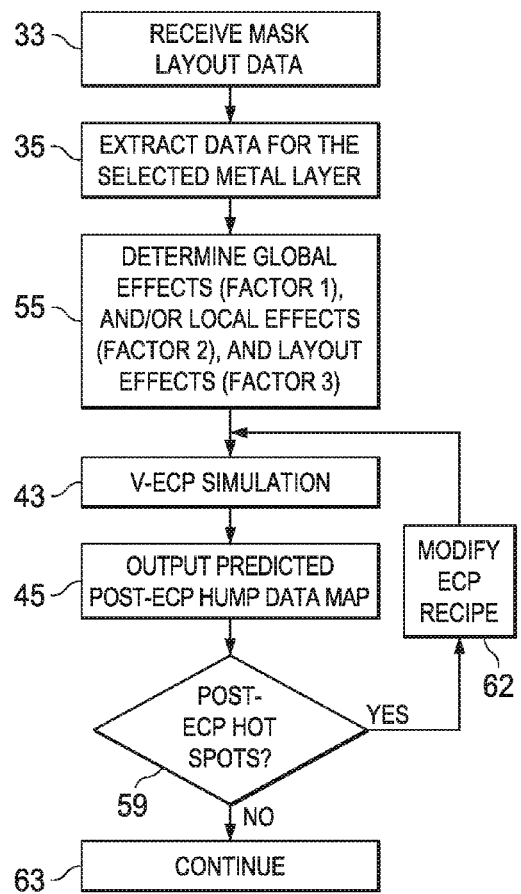
FIG. 8 depicts in a flow diagram an alternative method embodiment using the V-ECP simulator in an iterative method.

FIG. 8 depicts in a flow diagram an alternative method embodiment that also uses an iterative approach, when the ECP recipe is modified. Some steps of this method embodiment of FIG. 8 are common to the above described methods and like reference numerals are used for like steps. FIG. 8 also begins at step 33, where mask layout data such as GDSII formatted data is received for an entire wafer with metal layers to be produced using ECP/CMP processes. At step 35, the needed data is extracted for the selected metal layer in the IC design. At step 55, the three factors Factor 1, 2 and 3 are determined as described above for each unit grid area over the entire wafer. For simplicity, the steps 37, 39 and 41 of FIG. 6 above are not again described here, but are shown here as a single, combined step 55. At step 43, the V-ECP simulator is executed. A predicted post-ECP hump data map for the wafer is obtained in step 45. At step 59, a comparison is made for each pattern in the post-ECP hump data map in each unit grid area to a predetermined hump height threshold as in FIG. 3B above, and hot spots in the post-ECP hump data map are identified in unit grid areas where the threshold is exceeded.

If any hot spots are identified at step 59, then the method transitions to step 62, where the ECP recipe is modified. Unlike the embodiment of FIG. 7, here the layout pattern for the metal layer is left unmodified, although in an alternative embodiment both the layout and the ECP recipe can be modified. Instead, ECP recipe variables such as wafer rotation speed, current magnitude applied during plating, ECP solution chemistry, plating time, are changed to better optimize the predicted post-ECP hump height map. The process of FIG. 8 then transitions back to the V-ECP simulation at step 43, and continues using the new ECP recipe in the V-ECP simulation. This process of FIG. 8 is continued iteratively until the comparison at step 59 is negative, that is, until no hot spots are found in the predicted post-ECP hump height data map.

At step 63, the process continues, for example, by taking the predicted post-ECP hump data map from step 45 as an input to a V-CMP simulator. Alternatively, the photomask generation can be performed at this stage. In an embodiment, the method of FIG. 8 is performed for each metal layer in the design. Alternatively, the method is performed for selected metal layers.

Figures 9, 10:
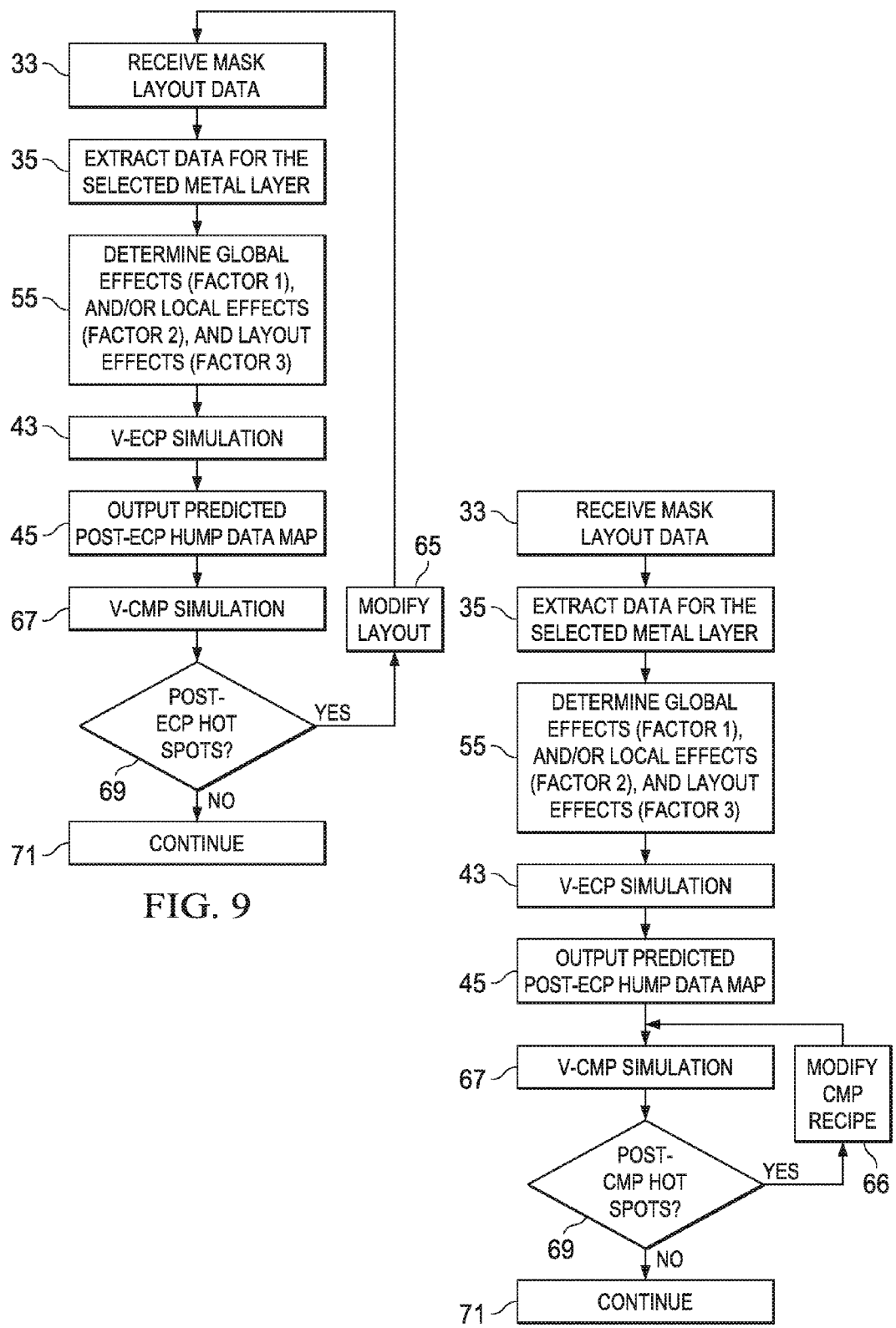
FIG. 9 depicts in a flow diagram yet another method embodiment using a V-CMP simulator in an iterative method.
FIG. 10 depicts in a flow diagram another alternative method embodiment using a V-CMP simulator.

FIG. 9 depicts yet another alternative method embodiment that uses an iterative approach and combines the V-ECP simulation with V-CMP simulations. In FIG. 9, some of the steps are the same as described above and like reference numerals are used for like elements.

The method in this embodiment starts at step 33, receiving mask layout data as before; in an example this is a GDSII format file that contains the data for each layer of the wafer. At step 35, the data needed for a particular metal layer is extracted. At step 55, the three factors, (at least one of the global effects factor, Factor 1 and the local effects factor, Factor 2, and the layout factor, Factor 3) are determined as described above for each unit grid over the entire wafer. At step 43, the V-ECP simulator is executed as described above, using the three factors as inputs. In an alternative embodiment, at least one of Factor 1, and Factor 2, is used with the third factor, Factor 3, in the V-ECP simulations. At step 45, the predicted post-ECP hump data map is obtained for the entire wafer. At step 67, V-CMP simulation is performed using the predicted post-ECP hump data map from step 45. A predicted post-CMP hump data map is output.

At step 69, a new comparison is done, comparing the predicted post-CMP hump data map to a predetermined post-CMP hump height threshold, and post-CMP hot spots are identified. This comparison is similar to that shown in FIG. 3B above, but is applied to a post-CMP hump data map. At step 65, if hot spots are located in the post-CMP hump data map, the layout for the particular metal layer is modified, and the method begins again at step 33, that is, the method of FIG. 9 is performed iteratively. If there are no hot spots identified at step 69, then the method continues at step 71.

At step 71, the post CMP comparison at step 69 indicates an acceptable result is obtained for the ECP and CMP processes for the selected metal layer. In an embodiment, the method of FIG. 9 is performed for each metal layer in an IC design to be formed on a semiconductor wafer. Alternatively, the methods of FIGS. 7 and 8 may be used for some layers, and combined with the method of FIG. 9. A photomask generation (PG) data file is then output. A photomask fabrication is then performed using the PG data, and the photomask may be used in a semiconductor process such as shown in FIG. 1.

FIG. 10 illustrates in another flow diagram yet another alternative method embodiment that optimizes a metal pattern layout using the predicted post-CMP hump height data map. In this embodiment, the method iteratively modifies the CMP recipe, instead of modifying the proposed layout as described above. Again several steps depicted in FIG. 10 are common to the method embodiments described above and like reference numerals are used. At step 33 the mask layout data is received as a data file for the entire wafer. At step 35, the data needed for the selected metal layer is extracted from the GDSII file. In step 55, the three factors Factor 1, Factor 2 and Factor 3, are determined, as described above, for each unit grid area. At step 43, the V-ECP simulation is again performed.

The predicted post-ECP hump data map is obtained from the V-ECP simulator at step 45. At step 67, the V-CMP simulation is now performed using the post-ECP hump data map as an input. The V-CMP simulator uses a correlated table based on experimental results and includes the CMP recipe information about the slurry type, pad type, arm position, rotation speed, and so forth. A predicted post-CMP hump data map is output. At step 69, the predicted post-CMP hump data map is compared to a predetermined post-CMP hump height threshold similar to the comparison shown in FIG. 3B above, and hot spots are identified in the predicted post-CMP data map. If hot spots—areas where the predicted post-CMP hump heights are above the threshold-are found in the predicted post CMP hump data map, then at step 66, the CMP recipe is modified. For example, the CMP process time, CMP pad pressure, or the CMP slurry type, or the CMP pad type could be modified.

In this embodiment of FIG. 10, the layout for the metal pattern for the selected metal layer is not modified; although as an alternative embodiment both the layout and the CMP recipe are modified. The V-CMP simulation may now be performed again at step 67. In other words, the process of modifying the CMP recipe, and V-CMP simulation, is performed iteratively. If at step 69, there are no hot spots in the post-CMP hump data map, the process continues at step 71, as above, to output the photomask generation data. In one embodiment, the method of FIG. 10 is performed for each metal layer to be used in an IC design. Alternatively, the method of FIG. 10 is performed for certain metal layers, but not necessarily for all metal layers in the design. The method embodiment of FIG. 10 is sometimes combined with the other embodiments in FIGS. 6-9 above.

In an example embodiment, the method embodiments are provided as executable computer instructions stored on a non-transitory computer readable medium, such as a non-volatile storage including hard drive, flash drive, floppy disk, USB, thumbdrive, compact FLASH card, server storage, solid state disk drive storage; particularly as executable instructions in either source code or compiled or assembly code formats, that when executed by a computing device, perform the embodiment methods as described above.

Figure 11:
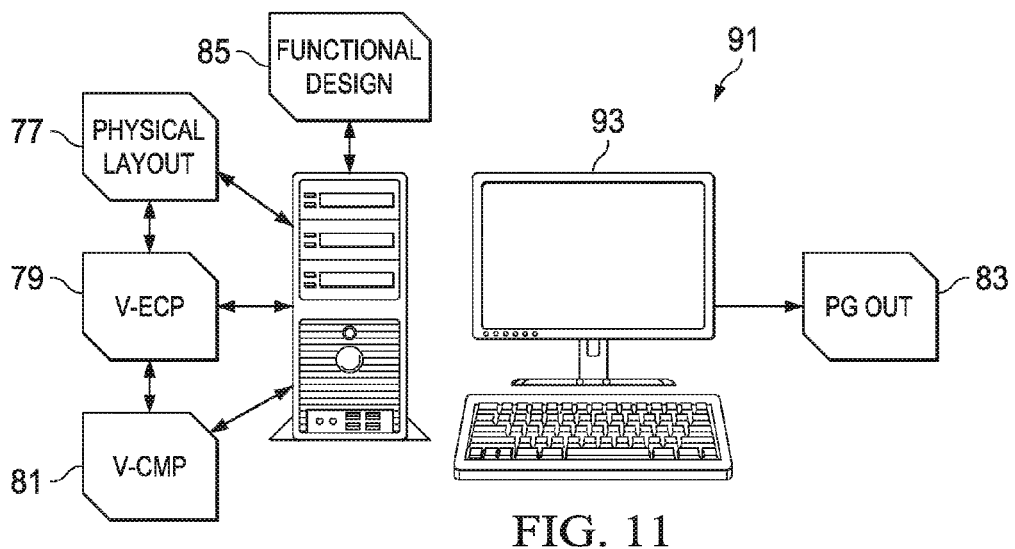
FIG. 11 depicts in a block diagram a computing device for use with the embodiments.

FIG. 11 depicts, in a simple block diagram, an example IC design and verification environment 91 for use with the embodiments. In FIG. 11, computing device 93 is shown. This device 93 is, as non-limiting examples, an engineering work station, a desktop computer, a laptop computer, a terminal interfaced to the internet or other network including storage, a tablet or portable computer device, a smartphone or other computing device for executing software. Software programs 85, 77 and V-ECP simulator 79 and V-CMP simulator 81 for use with computing device 93 are shown.

As described above, the simulators 79 (V-ECP) and 81 (V-CMP) are calibrated. For example, in order for the V-ECP simulator 79 to correctly perform a simulation on a proposed conductor pattern to be manufactured at a semiconductor processing facility, prior data collected from test runs and including parametric information about the ECP process, such as the plating bath chemistry, voltage, current, time, temperature used, and the results obtained by that particular process, are input to the V-ECP simulator 79. In an embodiment, a correlated data look up table is used to perform the simulation. V-ECP 79 may allow for user selection of different known recipes. Similarly, the V-CMP simulator 81 may also be calibrated to a particular semiconductor process and particular CMP tool. In one embodiment, a correlated data look up table with data from test wafers and recipes is used to perform the V-CMP simulation.

As shown in FIG. 11, a software tool 83 is used to perform a photomask generation or "PG" output data. This PG output data format can be used by a photomask fabrication facility to make the optical photomasks needed to form the conductors on a semiconductor wafer, such as photomask 22 in FIG. 1.

Note that the method embodiments shown above in FIGS. 6-10 can be performed for each metal layer in an IC design, or for selected metal layers. In this manner, each photomask to be used in production of the metal layers on a semiconductor wafer can be optimized for the ECP and CMP processes before the photomasks are manufactured. The embodiments are used singly or alternatively, used together in many combinations.

Advantages that are attained by use of the various embodiments include providing a layout for an IC to be formed on a semiconductor wafer that is optimized prior to manufacture using V-ECP and V-CMP simulators for each metal layer to be used, so that the results of ECP and CMP processes performed on the semiconductor wafer are known to be within acceptable limits for conductor height variation in the conductor thicknesses; and by use of the embodiments the ECP and CMP simulations performed are sufficiently accurate so that the photomasks produced after the method embodiments are performed will not need further modifications due to post-ECP or post-CMP hump height variations. By reducing or eliminating the need for iteratively producing many photomasks and test wafers to optimize an IC design, costs are reduced, and time is saved in the manufacturing process.

Through use of the embodiments, a computing device executing software programs including a V-ECP simulator that first calculates the factors for global effects, local effects, and layout effects for each unit grid area over the substrate as described above, and then performs the V-ECP simulation, outputting an accurate post-ECP hump data map, can be used to optimize a layout design for an IC. Modifications to the IC layout are made to improve the post-ECP results and also the post-CMP results prior to photomask manufacturing, and without the need for producing various versions of photomasks, and without the need for producing test wafers. Further, accurate V-ECP and V-CMP simulations may also be performed using the embodiments.

In an embodiment, a method includes receiving layout data for an IC design to be manufactured on a semiconductor wafer substrate with patterned conductors formed conductors in a metal layer formed in an electrochemical plating (ECP) process; extracting layout data from the received layout data corresponding to at least one the metal layer to be formed in the ECP process from the received layout data; determining from the extracted layout data a layout effects factor for each of a plurality of unit grid areas covering the semiconductor wafer, the layout effects factor corresponding to a pattern density for the at least one metal layer in the unit grid area; determining from the extracted layout data a global effects factor corresponding to a global pattern density of the patterned conductors for the at least one metal layer over a total area of the semiconductor wafer; determining from the extracted layout data a local effects factor for each of the unit grid areas, the local effects factor corresponding a local pattern density of the patterned conductors for the at least one metal layer over a total area of the semiconductor wafer within a local area larger than, and surrounding, the corresponding unit grid area; determining from the extracted data layout effect factors corresponding to the line width and line spacing for each of a plurality of unit grid areas dividing the semiconductor substrate; using a computing device, performing a virtual-ECP simulation configured to predict post-ECP plating hump heights in the at least one metal layer for each one of the unit grid areas, the virtual-ECP simulation using at least one of the global effects factor and the local effects factors, and also using the layout effects factor; outputting an predicted post-ECP hump data map for the semiconductor wafer from the virtual-ECP simulation; determining from the predicted post-ECP hump data map whether, for a selected whether pattern site on the semiconductor substrate, the predicted post-ECP pattern hump data map for the semiconductor wafer has a hump height that exceeds a predetermined hump height variance threshold; and responsive to the determining, modifying the layout data.

In another embodiment, in the above method, the method includes using the modified layout data and the computing device, outputting updated layout data for the IC design. In a further embodiment, in the above method, the method includes adding dummy conductor patterns for the at least one metal layer to the conductor patterns for the metal layer corresponding to the layout data. In still a further embodiment, in the above methods, the method includes using the computing device executing software, iteratively performing: determining the global effects factor, determining the local effects factors, determining the layout effects factor for each one of the unit grid areas, and executing the virtual-ECP simulation using each of the global effects factor, the local effects factors, and the layout effects factors; for each iteration, outputting an predicted post-ECP hump data map from the virtual-ECP simulation and determining from the predicted post-ECP hump data map whether, for a selected pattern site on the semiconductor substrate, the at least one metal layer over the semiconductor wafer will have a post-ECP hump height that exceeds a predetermined hump height threshold; and responsive to the determining, for each iteration, modifying the layout data.

In still another embodiment, in the above methods, the methods further include continuing the iteratively performing until the predicted post-ECP hump map hump height variance for any selected conductor pattern in for the semiconductor substrate wafer fails to have a hump height that exceeds the predetermined hump height threshold. In yet another embodiment, in the above methods, the methods include using the predicted post-ECP hump data map and the layout data, executing a virtual-chemical-mechanical polishing (virtual-CMP) simulation on a computing device to predict, for each unit grid area, an predicted post-CMP hump height; outputting an predicted post-CMP hump data map; and determining whether the predicted post-CMP hump data map has patterns in the at least one metal layer that exceed a predetermined CMP hump height variance threshold anywhere on the semiconductor wafer.

In yet another embodiment, the method includes modifying the layout data if the CMP hump height variance threshold is exceeded. In still another embodiment, the above method is performed and includes responsive to the determining, modifying a CMP recipe selected from a plurality of CMP recipes; and using the predicted post-ECP hump data map and the layout data and a computing device, executing the virtual-CMP simulation using the modified CMP recipe; outputting an predicted post-CMP hump height data map; and determining whether the post-CMP hump height data map for the semiconductor wafer has any patterns that exceed a predetermined post-CMP hump height threshold. In yet another embodiment, in the above methods, the methods include using a computing device, iteratively performing modifying a CMP recipe, executing a virtual-CMP simulation, outputting a predicted post-CMP hump data map, and determining steps, until the predetermined post-CMP hump height threshold is not exceeded.

In still another embodiment, in the above methods, the methods further include modifying an ECP recipe by selecting one from a plurality of predetermined ECP recipes; and using a computing device, executing the virtual-ECP simulation using the modified ECP recipe, and each of the global effects factor, the local effects factor and the layout effects factor for each unit grid area; outputting an predicted post-ECP hump data map; and determining from the predicted post-ECP hump data map whether, for a selected pattern site on the semiconductor substrate, the at least one metal layer for the semiconductor wafer will have a post-ECP hump height that exceeds a predetermined post-ECP hump height threshold.

In another further embodiment, in the above methods, the methods include wherein the virtual-ECP simulation uses all three of the global effects factor, the local effects factor and the layout effects factor in the simulation. In another embodiment, in the above methods, determining a layout global effects factor corresponding to a global pattern density of the patterned conductors includes using the computing device, for a unit grid area, calculating a line width over a sum of the line width and the line spacing for the at least one metal layer in the unit grid area. In yet another embodiment, in the above methods, determining the local effects factors for a plurality of local regions comprises, for each unit grid area, using the computing device, calculating the area of the at least one metal layer over a total surface area in each of the plurality of local region surrounding and including the corresponding unit grid area.

In another embodiment, in the above methods, determining the layout effects factors further comprises, for each one of the a plurality of unit grid areas covering the semiconductor wafer, using the computing device, calculating a reciprocal of a sum of the line width and the line spacing for conductor patterns in the at least one metal layer within the unit grid area.

In another example embodiment, a method includes using a computing device having a non-transitory computer memory storing executable programs, performing: retrieving from the non-transitory computer memory layout data for a design to be manufactured using an electrochemical plating (ECP) process forming patterned conductors in at least one metal layer over a semiconductor wafer; determining from the layout data, for each one of a plurality of unit grid areas covering the semiconductor wafer, a layout effects factor corresponding to a conductor pattern density in the at least one metal layer in the unit grid area; determining from the layout data a global effects factor corresponding to a global pattern density corresponding to which is a total area of the metal layer on the semiconductor wafer over a total area of the semiconductor wafers; determining from the layout data a local effects factors for each of the unit grid areas, the local effects factor a plurality of local regions, each local effect factor corresponding to a local pattern density which is the total area of the at least one metal layer over the surface area of a local area that is larger than and includes the corresponding unit grid area; determining from the layout data layout effect factors corresponding to the conductor pattern density which is the reciprocal of the line spacing added to the line width for the conductor pattern within each of a plurality of unit grid regions over the semiconductor substrate; using the computing device, executing a virtual-ECP simulation using at least one of the global effects factor and the local effects factors and also using the layout effects factor as inputs to determine an predicted post-ECP hump height of the at least one metal layer for each of the unit grid areas; storing in the non-transitory computer memory an predicted post-ECP hump data map for the semiconductor wafer from the virtual-ECP simulator; and determining from the predicted post-ECP hump data map whether, for a selected site in the semiconductor substrate, the at least one metal layer will have a post-ECP hump height on the semiconductor wafer that exceeds a predetermined post-ECP hump height threshold.

In yet another embodiment, the above method further includes storing in the non-transitory computer memory a hot spot data map, indicating locations on the semiconductor wafer substrate where the at least one metal layer has predicted post-ECP hump heights that exceed the predetermined post-ECP hump height threshold. In still another embodiment, the above method includes graphically displaying the hot spot data map as a two dimensional image on a human readable visual display coupled to the computing device. In yet a further embodiment, the above methods further include responsive to the determining, using the computing device to modify the layout data.

In yet another example embodiment, an embodiment includes a non-transitory computer readable medium containing executable instructions that, when executed by a computing device, cause the computing device to perform: retrieving from the non-transitory computer readable medium layout data for forming patterned conductors in at least one metal layer over a semiconductor wafer in an electrochemical plating (ECP) process; determining from the layout data a global effects factor corresponding to the total area in the at least one metal layer on the semiconductor wafer over a total area of the semiconductor wafer; determining from the layout data a layout effects factor for each of a plurality of unit grid areas covering the semiconductor wafer, the layout effects factor corresponding to the pattern density of the at least one metal layer; determining from the layout data a local effects factor for each unit grid area, each local effects factor corresponding to the total area of the at least one metal layer over the area of the semiconductor wafer in a local area that is larger than and includes the corresponding unit grid area; using the computing device, executing an ECP simulation using at least one of the global effects factor and the local effects factor, and also using the layout effects factor for each unit grid area to predict the post-ECP hump height of the at least one metal layer for each unit grid area; storing in the non-transitory computer readable medium an predicted post-ECP hump data map output from the ECP simulation; responsive to the post-ECP hump data map, modifying the layout for the at least one metal layer; and outputting a photomask generation file for the at least one metal layer.

Although illustrative embodiments and advantages have been described in detail, it should be understood that various changes, substitutions, and alterations can be made herein without departing from the spirit and scope of the embodiments as defined by the appended claims. For example, alternate materials, and varied orders of steps may be implemented.

Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized as alternative embodiments. Accordingly, the appended claims are intended to include within their scope such processes, machines, manufacture, compositions of matter, means, methods, or steps.

What is claimed is:

1. A method, comprising:
receiving layout data for an IC design to be manufactured on a semiconductor wafer with patterned conductors formed in an electrochemical plating (ECP) process;
extracting layout data from the received layout data corresponding to at least one metal layer;
determining from the extracted layout data a layout effects factor for each of a plurality of unit grid areas covering the semiconductor wafer, the layout effects factor corresponding to one selected from a line edge density and a pattern density for the at least one metal layer in the unit grid area;
determining from the extracted layout data a global effects factor corresponding to a global pattern density for the at least one metal layer over a total area of the semiconductor wafer;

determining from the extracted layout data a local effects factor for each of the unit grid areas, the local effects factor corresponding to a local pattern density for the at least one metal layer over an area of the semiconductor wafer within a local grid area larger than, and surrounding, the corresponding unit grid area;

using a computing device, performing an ECP simulation configured to predict post-ECP plating hump heights in the at least one metal layer for each one of the unit grid areas, the ECP simulation using at least one of the global effects factor and the local effects factor as inputs, and using the layout effects factor as an input; and outputting a predicted post-ECP hump data map for the semiconductor wafer from the ECP simulation.

2. The method of claim 1, and further comprising:

determining from the predicted post-ECP hump data map whether the predicted post-ECP hump data map for the semiconductor wafer has a hump height that exceeds a predetermined hump height threshold; and responsive to the step of determining from the predicted post-ECP hump data map whether the predicted post-ECP hump data map for the semiconductor wafer has a hump height that exceeds a predetermined hump height threshold, modifying the layout data corresponding to the at least one metal layer.

3. The method of claim 2, and further comprising:

using the modified layout data and the computing device, outputting updated layout data for the IC design.

4. The method of claim 3, and further comprising:

using the computing device executing software, iteratively performing:

determining the global effects factor, determining the local effects factor, determining the layout effects factor for each one of the unit grid areas, and executing the ECP simulation using at least one of the global effects factor and the local effects factor, and using the layout effects factor;

for each iteration, outputting a predicted post-ECP hump data map from the ECP simulation and determining whether the at least one metal layer over the semiconductor wafer will have a post-ECP hump height that exceeds a predetermined hump height threshold; and responsive to the step of determining whether the at least one metal layer over the semiconductor wafer will have a post-ECP hump height that exceeds a predetermined hump height threshold, for each iteration, modifying the layout data.

5. The method of claim 4 and further comprising continuing the iteratively performing until the predicted post-ECP hump map for the semiconductor wafer fails to have a hump height that exceeds the predetermined hump height threshold.

6. The method of claim 2, wherein modifying the layout data further comprises adding dummy conductor patterns for the at least one metal layer to the layout data.

7. The method of claim 1, and further comprising:

using the predicted post-ECP hump data map and the layout data, executing a CMP simulation on a computing device to predict, for each unit grid area, a predicted post-CMP hump height;

outputting an predicted post-CMP hump data map; and determining whether the predicted post-CMP hump data map has patterns in the at least one metal layer that exceed a predetermined CMP hump height threshold on the semiconductor wafer.

8. The method of claim 7, and further comprising modifying the layout data if the CMP hump height threshold is exceeded.

9. The method of claim 7, and further comprising:

responsive to step of the determining whether the predicted post-CMP hump data map has patterns in the at least one metal layer that exceed a predetermined CMP hump height threshold, modifying a CMP recipe selected from a plurality of CMP recipes; and using the predicted post-ECP hump data map and the layout data and a computing device, executing the CMP simulation using the modified CMP recipe;

outputting a predicted post-CMP hump data map; and determining whether the predicted post-CMP hump data map for the semiconductor wafer has any post-CMP hump height that exceeds a predetermined post-CMP hump height threshold.

10. The method of claim 1, and further comprising:

modifying an ECP recipe by selecting one from a plurality of predetermined ECP recipes; and using a computing device, executing the ECP simulation using the modified ECP recipe, and at least one of the global effects factor and the local effects factor and using the layout effects factor for each unit grid area;

outputting a predicted post-ECP hump data map; and determining from the predicted post-ECP hump data map whether the at least one metal layer for the semiconductor wafer will have a post-ECP hump height that exceeds a predetermined post-ECP hump height threshold.

11. The method of claim 1, wherein performing the ECP simulation further comprises using all of the global effects factor, the local effects factor and the layout effects factor in the ECP simulation.

12. The method of claim 1, wherein determining a layout effects factor comprises: using the computing device, for a unit grid area, calculating a surface area for the at least one metal layer over a total surface area in the unit grid area.

13. The method of claim 1, wherein determining the local effects factor comprises: for each unit grid area, using the computing device, calculating a surface area of the at least one metal layer over a total surface area in a local region surrounding and including the corresponding unit grid area.

14. The method of claim 1, wherein determining the layout effects factor further comprises, for each one of the unit grid areas covering the semiconductor wafer, using the computing device, calculating a reciprocal of a sum of line width and line spacing for conductor line patterns in the at least one metal layer within the unit grid area.

15. A method, comprising:

using a computing device having a non-transitory computer memory storing executable programs, performing:

retrieving layout data from the non-transitory computer memory for a design to be manufactured using an electrochemical plating (ECP) process forming patterned conductors in at least one metal layer over a semiconductor wafer;

determining from the layout data, for each one of a plurality of unit grid areas covering the semiconductor wafer, a layout effects factor corresponding to one selected from a line edge density and a conductor pattern density in the at least one metal layer in the unit grid area;

determining from the layout data a global effects factor corresponding to a total area of the metal layer on the semiconductor wafer over a total area of the semiconductor wafer;

determining from the layout data a local effects factor for each of the unit grid areas, the local effects factor corresponding to a local pattern density of the at least one metal layer over a surface area of a local area that is larger than and includes the corresponding unit grid area;

using the computing device, executing an ECP simulation using at least one of the global effects factor and the local effects factor as inputs, and using the layout effects factor as an input, to determine a predicted post-ECP hump height of the at least one metal layer for each of the unit grid areas;

storing in the non-transitory computer memory a predicted post-ECP hump data map; and determining from the predicted post-ECP hump data map whether the at least one metal layer will have a post-ECP hump height on the semiconductor wafer that exceeds a predetermined post-ECP hump height threshold.

16. The method of claim 15, and further comprising:

storing in the non-transitory computer memory a hot spot data map, indicating locations on the semiconductor wafer where the predicted post-ECP hump heights exceed the predetermined post-ECP hump height threshold.

17. The method of claim 16, and further comprising:

graphically displaying the hot spot data map as a two dimensional image representing the semiconductor wafer on a human readable visual display.

18. The method of claim 15 and further comprising:

responsive to the step of determining from the predicted post-ECP hump data map whether the at least one metal layer will have a post-ECP hump height on the semiconductor wafer that exceeds a predetermined post-ECP hump height threshold, using the computing device to modify the layout data.

19. The method of claim 18, wherein modifying the layout data further comprises adding dummy conductor patterns for the at least one metal layer to the layout data.

20. A non-transitory computer readable medium containing executable instructions that, when executed by a computing device, cause the computing device to perform:

retrieving layout data from the non-transitory computer readable medium for forming patterned conductors in at least one metal layer over a semiconductor wafer in an electrochemical plating (ECP) process;

determining from the layout data a global effects factor corresponding to a total area in the at least one metal layer on the semiconductor wafer over a total area of the semiconductor wafer;

determining from the layout data a layout effects factor for each of a plurality of unit grid areas covering the semiconductor wafer, the layout effects factor corresponding to a pattern density of the at least one metal layer;

determining from the layout data a local effects factor for each unit grid area, each local effects factor corresponding to the total area of the at least one metal layer over the area of the semiconductor wafer in a local area that is larger than and includes the corresponding unit grid area;

using the computing device, executing an ECP simulation using at least one of the global effects factor and the local effects factor, and using the layout effects factor for each unit grid area, to predict a post-ECP hump height of the at least one metal layer for each unit grid area;

storing in the non-transitory computer readable medium a predicted post-ECP hump data map output from the ECP simulation;

responsive to the post-ECP hump data map, modifying the layout for the at least one metal layer; and outputting a photomask generation file for the at least one metal layer.

* * * * *